US011246823B2

(12) United States Patent
Greaves et al.

(10) Patent No.: US 11,246,823 B2
(45) Date of Patent: Feb. 15, 2022

(54) MOLECULARLY IMPRINTED POLYMER OF SOL-GEL TYPE FOR SELECTIVELY TRAPPING ODOROUS MOLECULES

(71) Applicant: L'ORÉAL, Paris (FR)

(72) Inventors: Andrew Greaves, Magny-le-Hongre (FR); Franco Manfre, Le Perreux sur Marne (FR); Karsten Haupt, Compiègne (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/655,386

(22) PCT Filed: Dec. 16, 2013

(86) PCT No.: PCT/EP2013/076659
§ 371 (c)(1),
(2) Date: Jun. 25, 2015

(87) PCT Pub. No.: WO2014/102078
PCT Pub. Date: Jul. 3, 2014

(65) Prior Publication Data
US 2015/0342868 A1 Dec. 3, 2015

Related U.S. Application Data

(60) Provisional application No. 61/773,179, filed on Mar. 6, 2013.

(30) Foreign Application Priority Data

Dec. 26, 2012 (FR) ...................................... 1262781

(51) Int. Cl.
*A61K 8/898* (2006.01)
*A61Q 15/00* (2006.01)
*C08K 5/5415* (2006.01)
*C08G 77/26* (2006.01)
*C08G 77/32* (2006.01)
*C08G 77/06* (2006.01)

(52) U.S. Cl.
CPC .............. *A61K 8/898* (2013.01); *A61Q 15/00* (2013.01); *C08G 77/06* (2013.01); *C08G 77/26* (2013.01); *C08G 77/32* (2013.01); *C08K 5/5415* (2013.01); *A61K 2800/54* (2013.01); *A61K 2800/56* (2013.01); *A61K 2800/87* (2013.01)

(58) Field of Classification Search
CPC ................ A61K 8/898; A61K 2800/54; A61K 2800/56; A61K 2800/87; A61Q 15/00; C08G 77/06; C08G 77/26; C08G 77/32; C08K 5/5415
See application file for complete search history.

(56) References Cited

U.S. PATENT DOCUMENTS

| 3,792,068 | A | 2/1974 | Luedders et al. |
| 5,630,978 | A | 5/1997 | Domb |
| 5,932,199 | A | 8/1999 | Esser |
| 6,057,377 | A * | 5/2000 | Sasaki ..................... C03C 1/006 |
| | | | 210/656 |
| 6,255,421 | B1 | 7/2001 | Plochocka et al. |
| 6,649,212 | B2 | 11/2003 | Payne et al. |
| 6,916,465 | B2 | 7/2005 | Panzer et al. |
| 7,820,770 | B2 | 10/2010 | Schoeley et al. |
| 8,114,921 | B2 | 2/2012 | Poulton et al. |
| 8,679,859 | B2 | 3/2014 | Yan et al. |
| 9,956,542 | B2 | 5/2018 | Haupt et al. |
| 10,335,355 | B2 | 7/2019 | Greaves |
| 10,596,093 | B2 | 3/2020 | Greaves |
| 2003/0020049 | A1 | 1/2003 | Payne et al. |
| 2005/0063928 | A1 | 3/2005 | Withiam et al. |
| 2005/0084464 | A1 | 4/2005 | McGrath et al. |
| 2005/0084474 | A1 | 4/2005 | Wu et al. |

(Continued)

FOREIGN PATENT DOCUMENTS

| EP | 0925776 A2 | 6/1999 |
| EP | 0972512 A1 | 1/2000 |

(Continued)

OTHER PUBLICATIONS

Maitra et al. (Chemical Society Reviews, Published Aug. 2005, pp. 821-836).*
International Search Report for PCT/EP2013/077787, dated Feb. 17, 2014.
International Search Report for PCT/EP2013/076659, dated Apr. 10, 2014.
International Search Report for PCT/EP2013/076655, dated Mar. 18, 2014.
International Search Report for PCT/EP2013/077790, dated Apr. 11, 2014.

(Continued)

*Primary Examiner* — Alma Pipic
(74) *Attorney, Agent, or Firm* — The Marbury Law Group, PLLC

(57) ABSTRACT

The invention relates to the use of molecularly imprinted polymer(s) or MIPs, of odorous molecule(s), as deodorant agent in particular for selectively trapping molecules that are the cause of human body odour. More particularly by using MIPs which may be obtained via polymerization of "sol-gel" type; it being understood that the polymerization is performed in the presence v) of one or more "templates" of target molecule(s) responsible for human body odour. Another subject of the invention concerns a NI process for preparing MIPs as defined previously, MIPs obtained via this process, and a cosmetic composition comprising at least one MIP as defined previously. Unexpectedly, it appears that the MIPs make it possible to specifically trap precursors of odorous molecules and odorous molecules that may be used in cosmetic formulations, especially those that are the cause of the unpleasant odour of sweat.

19 Claims, No Drawings

(56) References Cited

U.S. PATENT DOCUMENTS

| | | |
|---|---|---|
| 2009/0148961 A1 | 6/2009 | Luchini et al. |
| 2009/0291058 A1 | 11/2009 | Woodland et al. |
| 2010/0048737 A1 | 2/2010 | Wendel et al. |
| 2010/0254932 A1 | 10/2010 | Benabdillah et al. |
| 2012/0100358 A1 | 4/2012 | Haupt et al. |
| 2013/0085186 A1 | 4/2013 | Wendel et al. |
| 2014/0076346 A1 | 3/2014 | Bourdin et al. |
| 2014/0205556 A1 | 7/2014 | Bourdin et al. |
| 2016/0106652 A1 | 4/2016 | Greaves |
| 2016/0143832 A1 | 5/2016 | Greaves |

FOREIGN PATENT DOCUMENTS

| | | | |
|---|---|---|---|
| EP | 1146057 A1 | 10/2001 | |
| EP | 1658863 A1 | 5/2006 | |
| JP | 2000-086446 A | 3/2000 | |
| WO | 2006/062926 A1 | 6/2006 | |
| WO | 2008/034764 A2 | 3/2008 | |
| WO | 2014/102077 A1 | 7/2014 | |
| WO | 2014/102206 A1 | 7/2014 | |
| WO | 2014/102209 A1 | 7/2014 | |

OTHER PUBLICATIONS

Non-Final Office Action for co-pending U.S. Appl. No. 14/655,395 (dated Jun. 17, 2016).

First Office Action for counterpart Chinese Application No. 201380068610.6, dated Mar. 4, 2016. (English translation).

Second Office Action for counterpart Chinese Application No. 201380068610.6, dated Oct. 8, 2016. (English translation).

Sangeetha, Neralagatta M. et al., "Supramolecular gels: Functions and uses," Chemical Society Reviews, published Aug. 2005, pp. 821-836.

Final Office Action for copending U.S. Appl. No. 14/655,395, dated Feb. 9, 2017.

Non-Final Office Action for copending U.S. Appl. No. 14/655,381, dated Apr. 27, 2017.

Obici, Silvana et al., "Central Administration of Oleic Acid Inhibits Glucose Production and Food Intake," Diabetes, vol. 51, Feb. 2002, pp. 271-275.

Non-Final Office Action for copending U.S. Appl. No. 14/655,390, dated May 3, 2017.

Final Office Action for copending U.S. Appl. No. 14/655,390, dated Jan. 25, 2018.

Non-Final Office Action for copending U.S. Appl. No. 14/655,395, dated Nov. 2, 2017.

Non-Final Office Action for copending U.S. Appl. No. 14/655,381, dated Feb. 16, 2018.

Non-Final Office Action for copending U.S. Appl. No. 14/655,390, dated Aug. 28, 2018.

Final Office Action for copending U.S. Appl. No. 14/655,395, dated Sep. 4, 2018.

Vasapollo, G., et al., "Molecularly Imprinted Polymers: Present and Future Prospective," International Journal of Molecular Sciences, 2001, 12, pp. 5908-5945.

Mayes et al., "Molecularly imprinted polymers: useful materials for analytical chemistry?," trends in analytical chemistry, vol. 16, No. 6, 1997, pp. 321-332.

Mujahid et al., "Chemical Sensors Based on Molecularly Imprinted Sol-Gel Materials," Materials 2010, 3, pp. 2196-2217.

Co-Pending U.S. Appl. No. 16/208,709, filed Dec. 4, 2018, entitled "Molecularly Imprinted Polymers of SOL-GEL Type and Their Use as Antidandruff Agent," Inventors: Andrew Greaves et al.

Final Office Action for copending U.S. Appl. No. 14/655,381, dated Oct. 9, 2018.

Final Office Action for co-pending U.S. Appl. No. 14/655,390, dated May 8, 2019.

Non-Final Office Action for co-pending U.S. Appl. No. 14/655,381, dated Jul. 1, 2019.

Non-Final Office Action for co-pending U.S. Appl. No. 16/208,709, dated Sep. 18, 2019.

Notice of Allowance for copending U.S. Appl. No. 14/655,381, dated May 5, 2020.

Final Office Action for copending U.S. Appl. No. 16/208,709, dated Jun. 5, 2020.

Non-Final Office Action for copending U.S. Appl. No. 16/208,709, dated Mar. 19, 2021.

Final Office Action for copending U.S. Appl. No. 16/208,709, dated Nov. 16, 2021.

\* cited by examiner

MOLECULARLY IMPRINTED POLYMER OF SOL-GEL TYPE FOR SELECTIVELY TRAPPING ODOROUS MOLECULES

This is a national stage application of PCT/EP2013/076659, filed internationally on Dec. 16, 2013, which claims priority to U.S. Provisional Application No. 61/773,179, filed on Mar. 6, 2013; as well as French Application 1262781, filed on Dec. 26, 2012, all of which are incorporated by reference herein in their entireties.

The invention relates to the cosmetic use of molecularly imprinted polymers (or MIPs) as agents for trapping molecule(s) that are at the surface of keratin materials, preferentially as deodorant agents, in particular for selectively trapping the odorous molecules or molecules responsible for human body odour, especially the one secreted by the skin. The invention also relates to MIPs which trap odorous molecules, to a composition comprising the said polymers and to a process for preparing the said polymers via "sol-gel" polymerization.

In the cosmetic field, it is known practice to use in topical application deodorant products containing active substances of bactericidal type to reduce or even eliminate the generally unpleasant underarm odours [see for example *Ullmann's Encyclopedia of Industrial Chemistry*, "Skin Cosmetics", G. Schneider et al., onlinelibrary.wiley.com/doi/10.1002/14356007.a24_219/pdf, published online on 15 Jan. 2001, Wiley-VCH, DOI: 10.1002/14356007.a24_219, point 8 "deodorants and Antiperspirants" (2012)].

Eccrine or apocrine sweat has little odour when it is secreted. It is its degradation by bacteria via enzymatic reactions that produces malodorous compounds.

The compounds which contribute towards unpleasant underarm odours comprise malodorous steroids, branched, saturated and/or unsaturated aliphatic volatile fatty acids, especially of $C_2$-$C_{12}$, and sulfanylalkanol compounds (*Chem. Biodivers.*, 1, 1058-1072, (2004)). Certain precursors of odorous substances and the mechanisms of generation thereof are described in the scientific literature [see for example *Journal of Investigative Dermatology*, 130, 529-540, (2010); *Int. J. Cosmet. Sci.*, 26, 149-156, (2004)].

Deodorant active agents have the function of reducing or preventing the formation of unpleasant odours. The various systems proposed hitherto may be principally grouped into four major families i) to iv):
  i) Bactericidal substances or substances that limit bacterial growth. Bactericides that destroy the resident bacterial flora. The most commonly used bactericides are Triclosan (2,4,4'-trichloro-2'-hydroxydiphenyl ether), chlorhexidine (1,6-bis(4-chlorophenylbiguanidino) hexane) and TTC (3,4,4'-trichlorocarbanilide). Among the substances that reduce bacterial growth, mention may be made of transition-metal chelating agents such as ethylenediaminetetraacetic acid (EDTA) or diethylenetriaminepentaacetic acid (DPTA);
  ii) Substances that block the enzymatic reactions responsible for the formation of odorous compounds. Mention may be made of arylsulfatase inhibitors, 5-lipoxygenase inhibitors, aminoacylase inhibitors and 3-glucuronidase inhibitors;
  iii) Unpleasant odour absorbers which "capture" or reduce the volatility of odorous compounds. Odour absorbers that may be mentioned include zeolites and cyclodextrins. It is also known that certain types of solid particles may be used as deodorants, such as the metal oxide silicates of patent application US 2005/063 928; the metal oxide particles modified with a transition metal in patent applications US 2005/084 464 and US 2005/084 474, aluminosilicates such as those described in patent application EP 1 658 863, nanometric chitosan-based particles such as those described in patent U.S. Pat. No. 6,916,465; and
  iv) Antiperspirants, including aluminium and/or zirconium salts, which are the most commonly used as active agents.

The principle of action of these active agents is considered to be the formation of a gel in the sweat duct. This gel creates a plug that partially blocks the sweat pores. The flow of sweat is thus reduced. These aluminium salts also have intrinsic efficacy since they are antibacterial agents. They thus also play a direct role on the deodorant efficacy by reducing the number of bacteria responsible for the degradation of sweat.

These various treatments applied to the skin especially of the armpits have a tendency to cause skin impairments reflected by irregularities and inhomogeneities such as pigmentary marks in particular on asiatic skin, dyschromia or blackheads often caused by regrowth of the hair.

At the present time, on the deodorant/antiperspirant products market, one of the main challenges is that of finding a solution for masking these irregularities immediately and noticeably by the consumer on application, while conserving a natural visual aspect. Furthermore, it is important to achieve this objective with materials that are compatible in deodorant/antiperspirant formulations and that do not result in large traces on clothing in contact with the skin.

Compositions based on deodorant active agents and/or antiperspirant active agents which are intended to be applied to the armpits after hair removal, for the purpose of hiding the marks caused by the hair-removal treatment (razor, wax or hair-removing cream), redness and blackheads, have already been proposed in Japanese patent application JP 2000-086 446. These compositions contain body powders such as talc, and organic or mineral dyestuffs.

Makeup compositions in particular for the face, comprising an antiperspirant active agent and a silicone elastomer, for improving the remanence of the colour distribution after application over time and for giving the complexion a matt effect that lasts for several hours, are also known in patent application EP 0 972 512. These compositions may comprise fillers intended to give body or rigidity to the composition, and/or softness, a matt effect and uniformity to the makeup. Among these fillers, use may be made of interference particles such as nacres, which are iridescent particles that reflect light, such as natural mother-of-pearl, mica coated with titanium oxide, with iron oxide, with a natural pigment or with bismuth oxychloride, or coloured titanium mica.

The problem of hiding skin irregularities caused by the treatment of deodorant/antiperspirant products is not mentioned in these documents.

There thus remains a real need for deodorant/antiperspirant products and for hiding skin impairments virtually immediately and/or noticeably by the consumer on application and which leave virtually no marks or even which are free of visible marks on clothing that is in contact with the skin.

Molecularly imprinted polymers or MIPs are materials that are widely used for their applications in the fields of biotechnology, chemistry, chromatography, analytical chemistry and biology (*J. Mol. Recognit.*, 19, 106-180 (2006); *Molecularly Imprinted Materials: Science and Technology*, Marcel Dekker, NY, M. Yan and O. Ramstrom (2005)). The concept of molecular imprinting relates to Emil Fisher's famous "lock and key fit" principle known since 1894 for enzymes with their ligand (*Advances in Carbohydrate Chemistry and Biochemistry*, 1-20 (1994)). Molecular imprinting consists more specifically in making a polymer comprising specific cavities in the shape and size of a target molecule or "imprint", from a "template" molecule which serves as a model for the formation of recognition sites for the target molecule, having shape complementarity with the template serving for the formation of the said specific cavities.

Molecularly imprinted polymers are polymers prepared from functional monomers polymerized around the said template. The monomer is thus chosen so as to develop interactions with the said template, which may be covalent or non-covalent, usually non-covalent, i.e. a) hydrogen bonding, b) electrostatic interactions, c) ionic interactions, and nonionic interactions or even low-energy interactions such as d) Van der Waals bonds, e) hydrophobic-hydrophobic interactions and f) interactions of π-π stacking types. The polymerization then takes place in a porogenic solvent between the monomers complexed with the template and a crosslinking agent so as to form specific cavities. The bonds or interactions between the template and the monomers are then broken by means of suitable solvents to extract the template from the polymer support.

Extraction of the said template then leaves vacant recognition sites with high affinity for the target molecule. The shape and size of the imprint and the spatial arrangement of the functional groups within the recognition cavity are complementary to the template molecule and contain specific sites for interaction with the target molecule.

This type of selective trapping is described in several scientific articles (see for example *Analytical Chemistry* "Molecularly imprinted polymers: the next generation", 75(17), 376-383, (2003); *Chemical Engineering Journal*, "Selective separation of basic and reactive dyes by molecularly imprinted polymers (MIPs)", 149(1-3), 263-272, (2009), *Kirk-Othmer Encyclopedia of Chemical Technology*, "Molecular Imprinting", D. Spivak; accessible online since 25 Jun. 2010, DOI: 10.1002/0471238961.molespiv.a01; Molecularly Imprinted Polymers; B. R. Hart, K. J. Shea, onlinelibrary.wiley.com/doi/10.1002/0471216275.esm054/full, *Encyclopedia of Polymer, Science and Technology*, accessible online since 15 Jul. 2002; DOI: 10.1002/0471216275.esm054; J. Sep. Sci, M. Lasàkovà, P. Jandera, 32, 799-812; *Int. J*. Mol. Sci., 7, 155-178 (2006)).

A study conducted on an MIP prepared using a testosterone-based template shows the importance of the positioning of the two hydrogen bonding donor and acceptor sites of this imprint molecule for the subsequent recognition of analogue molecules [see *J. Polymer Science: Part A: Polymer Chemistry*, S- H Cheong et al., 36, 1725 (1998)].

These MIPs have never been used as alternative deodorant agents.

The technical problems mentioned previously have been solved by the cosmetic use of molecularly imprinted polymer(s) or MIPs as agents for trapping molecule(s) that are at the surface of keratin materials and in particular the human skin; more particularly via the use of molecularly imprinted polymer(s) or MIPs for odorous molecule(s) and/or molecule(s) responsible for body odour, as deodorant agents, in particular for selectively trapping the molecules responsible for human body odour, it being understood that:
  the MIP(s) are obtained by polymerization of "sol-gel" type, and the sol-gel polymerization is performed in the presence of one or more "template(s)" of target molecule(s) that are at the surface of keratin materials, the template(s) advantageously being chosen from odorous molecules and molecules responsible for human body odour such as those of sweat and sebum.

Preferably, the MIP(s) of the invention contain one or more silanes.

Another subject of the invention concerns a process for preparing MIPs as defined previously, and MIPs obtained via this process and a cosmetic composition comprising at least one MIP as defined previously.

A subject of the invention is also a cosmetic process for treating keratin materials, especially the skin, against body odour and/or the molecule(s) responsible for odours, characterized in that at least one composition as defined is applied to the surface of the said materials.

It appears, unexpectedly, that MIPs can specifically trap molecules that are at the surface of keratin materials, especially the skin. More particularly, the MIPs of the invention can trap the precursors of odorous molecules and odorous molecules which may be used in cosmetic formulations, especially those which are the cause of unpleasant human body odour especially of sweat and sebum.

These MIPs can significantly reduce or eliminate human body odour, in particular underarm odour.

For the purposes of the present invention, and unless otherwise indicated, the following definitions apply:
  a "hydrocarbon-based chain" is "unsaturated" when it comprises one or more double bonds and/or one or more triple bonds;
  the "aryl" or "heteroaryl" radicals or the aryl or heteroaryl part of a radical may be substituted with at least one substituent borne by a carbon atom, chosen from:
    a $C_1$-$C_{16}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
    a halogen atom such as chlorine, fluorine or bromine;
    a hydroxyl group;
    a $C_1$-$C_2$ alkoxy radical;
    a $C_2$-$C_4$ (poly)hydroxyalkoxy radical;
    an amino radical;
    nitro or nitroso;
    a 5- or 6-membered heterocycloalkyl radical;
    an optionally cationic 5- or 6-membered heteroaryl radical, preferentially imidazolium, optionally substituted with a ($C_1$-$C_4$)alkyl radical, preferentially methyl;
    an amino radical substituted with one or two $C_1$-$C_6$ alkyl radicals, which may be identical or different, optionally bearing at least: i) a hydroxyl group, ii) an amino group optionally substituted with one or two optionally substituted $C_1$-$C_3$ alkyl radicals, the said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

an acylamino radical (—N(R)—C(O)R') in which the radical R is a hydrogen atom or a $C_1$-$C_4$ alkyl radical optionally bearing at least one hydroxyl group and the radical R' is a $C_1$-$C_2$ alkyl radical;

a carbamoyl radical ($(R)_2$N—C(O)—) in which the radicals R, which may be identical or different, represent a hydrogen atom or a $C_1$-$C_4$ alkyl radical optionally bearing at least one hydroxyl group;

a carboxylic acid or ester radical, (—O—C(O)R') or (—C(O)OR'), in which the radical R' is a hydrogen atom or a $C_1$-$C_4$ alkyl radical optionally bearing at least one hydroxyl group, and the radical R' is a $C_1$-$C_2$ alkyl radical;

the carboxylic radical possibly being in acid or salified form (preferably with an alkali metal or a substituted or unsubstituted ammonium);

an alkylsulfonylamino radical (R'S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;

an aminosulfonyl radical (($R)_2$N—S(O)$_2$—) in which the radicals R, which may be identical or different, represent a hydrogen atom or a $C_1$-$C_4$ alkyl radical optionally bearing at least one hydroxyl group;

a cyano group (CN);

a (poly)haloalkyl group, preferably trifluoromethyl ($CF_3$);

the cyclic or heterocyclic part of a non-aromatic radical of heterocycloalkyl type may be substituted with at least one substituent borne by a carbon atom, chosen from the groups:

hydroxyl;

$C_1$-$C_4$ alkoxy or $C_2$-$C_4$ (poly)hydroxyalkoxy;

alkylcarbonylamino ((RC(O)—NR'—) in which the radical R' is a hydrogen atom or a $C_1$-$C_4$ alkyl radical optionally bearing at least one hydroxyl group, and the radical R is a $C_1$-$C_2$ alkyl radical or an amino radical substituted with two $C_1$-$C_4$ alkyl groups, which may be identical or different, optionally bearing at least one hydroxyl group, the said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy ((RC(O)—O—) in which the radical R is a $C_1$-$C_4$ alkyl radical or an amino radical substituted with two identical or different $C_1$-$C_4$ alkyl groups optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl ((RO—C(O)—) in which the radical R is a $C_1$-$C_4$ alkyl radical or an amino radical substituted with two identical or different $C_1$-$C_4$ alkyl groups optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, may also be substituted with one or more oxo groups;

an "aryl" radical represents a fused or non-fused monocyclic or polycyclic group containing from 6 to 22 carbon atoms, and in which at least one ring is aromatic; in particular, the aryl radical is a phenyl, biphenyl, naphthyl, indenyl, anthracenyl or tetrahydronaphthyl and more preferentially phenyl or tetrahydronaphthyl;

a "heteroaryl" radical represents a 5- to 22-membered, monocyclic or polycyclic fused or non-fused group, comprising from 1 to 6 heteroatoms chosen from a nitrogen, oxygen, sulfur and selenium atom, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazinyl, pyrazinyl, pyrazolyl, pyridyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof;

a "cyclic" radical is a "cycloalkyl" radical, i.e. a non-aromatic, monocyclic or polycyclic, fused or non-fused radical, containing from 5 to 22 carbon atoms, which may comprise one or more unsaturations, such as cyclohexyl or cyclopentyl;

a "heterocyclic" or "heterocycloalkyl" radical is a non-aromatic, monocyclic or polycyclic, fused or non-fused 5- to 22-membered radical, comprising from 1 to 6 heteroatoms chosen from nitrogen, oxygen, sulfur and selenium atoms, morpholinyl, thiomorpholinyl, piperidyl, piperazinyl, pyrrolidinyl, tetrahydrofuryl, tetrahydrothiophenyl, azepanyl, thioazepanyl; preferentially pyrrolidinyl and morpholino;

an "alkyl" radical is a linear or branched $C_1$-$C_{16}$ and preferably $C_1$-$C_8$ hydrocarbon-based radical; particularly $C_1$-$C_4$ such as methyl or ethyl;

an "alkenyl" radical is a linear or branched $C_2$-$C_{20}$ hydrocarbon-based radical comprising one or more conjugated or unconjugated double bonds, in particular a $C_4$-$C_{10}$ radical comprising one, two or three double bonds, preferentially only one double bond;

the term "optionally substituted" attributed to the alkyl or alkenyl radical means that the said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, the said alkyl radicals possibly forming, with the nitrogen atom that bears them, a 5- to 7-membered heterocycle, optionally comprising another nitrogen or non-nitrogen heteroatom, v) phenyl, vi) ($C_1$-$C_6$)alkoxycarbonyl, vii) ($C_1$-$C_6$)alkylcarbonyloxy, viii) H—C(O)—O—;

an "alkoxy" radical is an alkyl-oxy or alkyl-O— radical for which the alkyl radical is a linear or branched $C_1$-$C_{16}$ and preferentially $C_1$-$C_8$ hydrocarbon-based radical; particularly $C_1$-$C_4$ such as methoxy or ethoxy, and when the alkoxy group is optionally substituted, this means that the alkyl group is optionally substituted as defined above;

a "(poly)haloalkyl" radical is an "alkyl" radical as defined previously, in which one or more hydrogen atoms are substituted or replaced with one or more halogen atoms such as the fluorine, chlorine or bromine atom; a polyhaloalkyl that may be mentioned is the trifluoromethyl group;

an "alkylthio" radical is a radical alkyl-S— for which the alkyl radical is a linear or branched $C_1$-$C_{16}$ and preferentially $C_1$-$C_8$ hydrocarbon-based radical; particularly $C_1$-$C_4$ such as methylthio or ethylthio, and when the alkylthio group is optionally substituted, this means that the alkyl group is optionally substituted as defined above;

an anionic counterion is organic or mineral, preferentially chosen from halide anions such as $Cl^-$, $Br^-$ or $I^-$, and organic anions such as mesylates;

when the expression "at least one" is used, "one or more" is implied;

the limit values delimiting the extent of a range of values are included in this range of values.

In the context of the present invention, the term "deodorant active agent" means any active agent which, by itself, has the effect of masking, absorbing, improving and/or reducing the unpleasant odour resulting from the decomposition of human sweat.

The term "antiperspirant active agent" means any substance which, by itself, has the effect of reducing the flow of sweat, of reducing the sensation on the skin of moisture associated with human sweat and of masking human sweat.

The "supports" for the MIPs

The retention of the support for the MIPs with the said template is based on a molecular recognition mechanism in the functional monomer "pre-organized" and polymerized around the said template of odorous molecule(s) and/or of target molecule(s) responsible for human body odour.

Sol-Gel Polymerization

The polymerization method used for manufacturing the MIPs according to the invention is polymerization via the process known as "sol-gel" polymerization.

The sol-gel process makes it possible to manufacture a mineral polymer via simple chemical reactions known to those skilled in the art (see, for example, Kirk-Othmer Encyclopedia of Chemical Technology "Sol-Gel Technology", A. C. Pierre, placed online on 13 Jul. 2007, DOI: 10.1002/0471238961.19151208051403.a01.pub2; onlinelibrary.wiley.com/doi/10.1002/0471238961.19151208051403.a01.pub2/pdf and *Ullmann's Encyclopedia of Industrial Chemistry*, "Aerogels" N. Hüsing and U. Schubert, placed online on 15 Dec. 2006, DOI: 10.1002/14356007.c01_c01.pub2: onlinelibrary.wiley.com/doi/10.1002/14356007.c01_c01.pub2/pdf).

During the transformation of the reaction medium, the viscosity increases, passing from a "sol", which is defined as being a colloidal suspension of very small particles, to a porous, rigid network known as a "gel".

"Sol-gel" polymerization may take place with precursors other than silanes, such as titanates, aluminates or mixtures.

Advantageously, the polymerization is performed using alkoxides having the formula $M'(R_7)_n$ with M' representing a metal or a silicon atom Si; n is an integer preferably greater than 2, and $R_7$ represents i) an optionally substituted, preferably unsubstituted, linear or branched ($C_1$-$C_{30}$)alkyl group or ii) a linear or branched ($C_1$-$C_{30}$)alkoxy group, which is optionally substituted, preferably with an amino group $N(H)R_d$ with $R_d$ representing a hydrogen atom or a ($C_1$-$C_6$)alkyl group, it being understood that at least one radical $R_7$ represents an alkoxy group as defined previously. These alkoxide precursors may be in liquid or solid form; when they are solid, they are preferentially soluble in common solvents, in particular in cosmetically acceptable solvents.

According to a preferred mode of the invention, the MIP(s) of the invention prepared via the sol-gel technique are chosen to form stable complexes between the MIP and the template via low-energy interactions such as non-covalent bonds, i.e. hydrogen bonds, electrostatic bonds or Van Der Waals interactions.

To synthesize a molecularly imprinted polymer of "sol-gel" type, use may be made of precursors bearing hydrolysable functions generating the silicate network and bearing organic functions which remain grafted to the mineral backbone. The organic functions may then interact with the template during the synthesis and aid the formation of the specific cavities in the network.

More particularly, the MIP(s) of the invention are prepared from silane of formula (I) below:

$$R_1Si(OR_2)_z(R_3)_x \qquad (I)$$

in which formula (I):

$R_1$ represents a linear or branched, saturated or unsaturated, cyclic or acyclic $C_1$-$C_6$ hydrocarbon-based chain, which is optionally substituted, preferably with a group chosen from the following groups:

amine $NH_2$ or NHR with R representing a $C_1$-$C_4$ alkyl group, an aryl or aryloxy group, which is optionally substituted, especially with an amino group or with a $C_1$-$C_4$ aminoalkyl group, $R_1$ possibly being interrupted in its chain with a heteroatom (O, S, NH), a carbonyl group —C(O)— or a combination thereof, R, being linked to the silicon atom directly via a carbon atom, $R_2$ and $R_3$, which may be identical or different, represent a linear or branched alkyl group comprising from 1 to 6 carbon atoms, z denotes an integer ranging from 1 to 3, and x denotes an integer ranging from 0 to 2, with z+x=3.

Preferably, the compounds of formula (I) are such that $R_2$ represents an alkyl group comprising from 1 to 4 carbon atoms, particularly a linear group comprising from 1 to 4 carbon atoms. More particularly, $R_2$ represents an ethyl group.

In particular, $R_1$ is an acyclic chain. Preferably, $R_3$ represents an alkyl group comprising from 1 to 4 carbon atoms.

According to a variant, the compounds of formula (I) are such that $R_3$ represents a linear alkyl group comprising from 1 to 4 carbon atoms, and, preferably, $R_3$ represents a methyl group.

Preferably, z is equal to 3 and x=0.

According to an advantageous variant, the compounds of formula (I) are such that $R_1$ represents a linear or branched, saturated or unsaturated $C_1$-$C_6$ hydrocarbon-based chain, substituted with an amine group $NH_2$ or NHR (R=$C_1$-$C_6$ alkyl, $C_3$-$C_6$ cycloalkyl or $C_6$ aromatic). Preferentially, $R_1$ is a saturated linear $C_1$-$C_6$ hydrocarbon-based chain substituted with an amine group $NH_2$. More preferentially, $R_1$ is a saturated linear $C_2$-$C_4$ hydrocarbon-based chain substituted with an amine group $NH_2$.

According to a particular variant of the invention, the sol-gel process uses functional silane monomers of formula (II) below:

$$R_9-Si(OR_8)_z(R'_8)_x \qquad (II)$$

in which formula (II):

$R_8$ and $R'_8$, which may be identical or different, represent i) a hydrogen atom, ii) a linear or branched, optionally substituted $(C_1-C_8)$alkyl group, preferably, the group $R_8$ is a $(C_1-C_4)$ alkyl group such as methyl or ethyl and $R_9$ represents i) a hydrogen atom, ii) a group $OR_8$ as defined previously, and iii) a linear or branched $(C_1-C_6)$alkyl group, which is optionally substituted, in particular with a thiol or hydroxyl group or with an amino group $N(H)R_d$ with $R_d$ representing a hydrogen atom or a $(C_1-C_6)$alkyl group such as aminoethyl, iv) a (hetero)aryl group such as phenyl, or v) (hetero)aryl $(C_1-C_6)$alkyl such as benzyl, z=1, 2, 3 and x=0, 1, 2 with z+x=3.

The synthesis of this polymer is performed using chemical reactions known to those skilled in the art, which are started when the reagents are placed in contact with water and optionally with a catalyst (acidic or basic), which has the effect 1) of hydrolyzing the alkoxy groups ($OR_8$) of the silanes into hydroxyl, and then 2) of condensing with the hydrolyzed products to lead 3) to polymerization or gelation of the system [see *Kirk-Othmer Encyclopedia of Chemical Technology* "Sol-Gel Technology", and *Ullmann's Encyclopedia of Industrial Chemistry*, "Aerogels" referenced above; and *Molecularly imprinted polymers—Man-made mimics of antibodies and their applications in analytical chemistry*. Techniques and instrumentation in analytical chemistry, B. Sellergren, i.t.i.a. chem. Amsterdam, Elsevier Ed, Vol. 23 (2001)].

A catalyst may be introduced into the reaction medium to accelerate the condensation reaction. Mention may be made of the articles Catalysts and the structure of $SiO_2$ sol-gel films, *Journal Of Materials Science*, 35 1835-184 (2000) and *Sol-gel processing of silica: II. The role of the catalyst*, *Journal of Non-Crystalline Solids*, 87, Issues 1-2, 185-198 (2 Oct. 1986) and the articles cited in these articles which mention catalysts used for catalyzing the sol-gel reaction, which may be used in the present invention.

According to another advantageous variant, the MIP of the invention is synthesized via the sol-gel method with an acidic catalyst or an acidifying agent. The term "acidifying agent" in particular means mineral acids such as hydrochloric acid or organic acids, in particular carboxylic acids such as acetic acid. Preferably, the acidic catalyst is added at the start of the reaction.

According to a preferred mode of the invention, the sol-gel process uses a catalyst, especially a basic catalyst or a basifying agent as defined below.

According to a particular embodiment of the invention, a basic catalyst is added, preferably in a large excess of water, preferentially at the end of the reaction.

The process of the invention for obtaining MIPs via the sol-gel process is particularly performed at a temperature inclusively between 20 and 150° C.

Preferentially, the "sol-gel" polymerization is performed using functional silane monomers, in particular aryltri($C_1$-$C_6$)alkoxysilanes such as phenyltrimethoxysilane (PTMOS), (amino)($C_1$-$C_6$)(alkyl)tri($C_1$-$C_6$)alkoxysilanes such as aminopropyltriethoxysilane (APTES) or bis($C_1$-$C_6$)tri($C_1$-$C_6$) alkoxysilyl ($C_1$-$C_6$)alkyl)aryl such as bis(trimethoxysilylethyl)benzene (BTEB) optionally combined with an acrylate-based monomer such as poly(2,2,3,4,4,4-hexafluorobutyl acrylate) (polyHFBA); or 2-(trimethoxysilylethyl) pyridine (TMSE-Pyr), the functional monomer(s) optionally being in contact with a crosslinking agent of the tetra($C_1$-$C_6$)alkoxysilane family such as tetraethoxysilane (TEOS), tetramethoxysilane (TMOS), mercapto($C_1$-$C_6$)alkyltri($C_1$-$C_6$)alkoxysilanes such as mercaptopropyltrimethoxysilane (MPTMS) and ($C_1$-$C_6$)alkyltri($C_1$-$C_6$)alkoxysilanes such as methyltrimethoxysilane (C1-triEOS). The functional monomers bearing a (hetero)aryl group of aryltri($C_1$-$C_6$)alkoxysilane type are particularly suitable for template molecules comprising at least one aromatic group such as phenyl.

According to a particularly advantageous variant, the silane of formula (I) or (II) as defined previously is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl) phenethyltrimethoxysilane. Preferably, the silane (I) is chosen from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane.

More preferentially, the polymerization of "sol-gel" type of the invention is performed using (amino)trialkoxysilane functional monomers of aminopropyltriethoxysilane (APTES) type in the presence of a crosslinking agent such as tetraethoxysilane (TEOS).

According to a particular embodiment of the invention, the sol-gel polymerization is performed in the presence of basifying agent(s) as defined below, preferentially in the presence of aqueous ammonia.

More particularly, the process for preparing molecularly imprinted polymer(s) or MIPs, of odorous molecules via polymerization of "sol-gel" type using:

i) one or more functional monomers as defined previously, preferably APTES;

ii) optionally one or more crosslinking agents as defined previously, preferably TEOS; and iii) one or more porogenic solvents as defined below, preferably a polar protic solvent such as ethanol and/or water;

iv) one or more templates, in particular one or more odorous molecules or molecules responsible for body odour as defined below;

v) optionally one or more polymerization catalysts, preferably a basifying agent, in particular aqueous ammonia.

The polymerization is advantageously followed by a step of removing the template present in the MIP obtained after the polymerization step.

The removal step may be performed in the following manner:

At the end of the synthesis of the sol-gel, the reaction mixture is preferentially treated to recover the MIP still containing the template. The standard techniques known to those skilled in the art, such as centrifugation or filtration (optionally preceded by a precipitation step), may be used to recover the MIP still containing the template. The gel obtained is optionally dried at temperatures between room temperature 25° C. and 150° C., optionally under vacuum. Preferably, the gel is used without drying. The gel is washed to extract the template with one or a mixture of polar protic solvent(s) such as ethanol, water, acetic acid; solutions of polar protic solvents such as ethanol and water basified with basifying agents such as aqueous ammonia and sodium hydroxide; solutions of polar protic solvents such as ethanol and water acidified with acidifying agents such as acetic acid and hydrochloric acid. Optionally, the gel is washed to remove the excess of the extraction solvent and residual monomers with one or a mixture of polar (a)protic solvent(s) such as ethanol or acetone. The gel is finally dried.

An alternative consists in washing the gel to remove the excess extraction solvent and residual monomers with one or a mixture of polar (a)protic solvent(s) such as ethanol or acetone, followed by washing to extract the template with one or a mixture of polar protic solvent(s) such as ethanol, water, acetic acid; solutions of polar protic solvent(s) such as ethanol and water basified with basifying agents such as aqueous ammonia and sodium hydroxide; solutions of polar protic solvent(s) such as ethanol and water acidified with acidifying agents such as acetic acid and hydrochloric acid. The gel is finally dried.

Another alternative consists in washing the gel to remove the excess of the extraction solvent and residual monomers with one or a mixture of polar (a)protic solvent(s) such as ethanol or acetone, followed by washing to extract the template with one or a mixture of polar protic solvent(s) such as ethanol, water, acetic acid; solutions of polar protic solvent(s) such as ethanol and water basified with basifying agents such as aqueous ammonia and sodium hydroxide; solutions of polar protic solvent(s) such as ethanol and water acidified with acidifying agents such as acetic acid and hydrochloric acid. The gel is washed to remove the excess of the extraction solvent and residual monomers with one or a mixture of polar (a)protic solvent(s) such as ethanol or acetone.

The drying process of the invention makes it possible to obtain the sol-gel material preferentially making it necessary for the washing solvents to be able to escape at the same time that the gel solidifies.

The drying used in the process for preparing the MIPs of the invention is either standard drying (normal evaporation optionally preceded by recovery of the gel via the standard techniques known to those skilled in the art, such as centrifugation or filtration) or drying under supercritical conditions. Mention may be made of the articles Dossier Technique: Le Procédé Sol-Gel du Rescoll Centre Technologique (rescoll.fr/blog/wp-content/uploads/2009/04/dossier-technique-sol-gel-blog-rescoll1.pdf) and The sol-gel process, Chem. Rev., 90 (1), 33-72 (1990). Preferably, the gel is dried under vacuum between room temperature and 100° C.

According to a particular mode of the invention, the process for preparing molecularly imprinted polymer(s) or MIPs, of odorous molecule(s) via polymerization of "sol-gel" type is performed using:

i) one or more functional monomers as defined previously;
ii) one or more crosslinking agents as defined previously; and
iii) one or more porogenic solvents as defined previously;
iv) one or more odorous molecules as defined previously; and
v) one or more basifying agents as defined previously;
vi) optionally one or more acids;

it being understood that the ingredients i), ii), iii), iv) and vi) are first mixed together and v) is then added; the mixture i) to vi) is preferably prepared:

at room temperature (25° C.), at atmospheric pressure, for at least one hour, preferably between 2 hours and 48 hours and in particular between 3 hours and 24 hours, followed by washing with one or a mixture of polar (a)protic solvent(s) such as ethanol or acetone, optionally dried, preferably in air, and then purified by washing with one or a mixture of polar protic solvent(s) such as ethanol or a carboxylic acid such as acetic acid, followed by at least one wash as defined previously, and then drying as defined previously.

It is understood that the "sol-gel" MIP preparation according to the invention takes place in the presence of water.

The Imprint Molecules or Template

The aim of the invention is to provide a polymer of MIP type which takes up molecules that are at the surface of keratin materials, preferentially odorous molecules or molecules that are the source of unpleasant human body odour such as those of sweat and sebum.

As seen previously, the "template" is a compound which mimics the molecules that are the cause of the said odours within the MIP in order for the MIP to be able subsequently to take up the odours. The template must therefore be representative of the odorous molecules targeted or of the molecules which are the source of the odours in the sample. The resemblance between the template and the sought molecules must relate equally to their size and shape and to the nature, position and spatial orientation of their functional groups.

These molecules or templates are preferentially chosen from:

a) linear or branched, saturated or unsaturated, and/or optionally substituted $C_2$-$C_{13}$ aliphatic acids such as those of formula (T1) below:

$$R^{11}\text{---C(O)---OH} \tag{T1}$$

in which formula (T1) $R^{11}$ represents i) a linear or branched $(C_1$-$C_{13})$alkyl group which is optionally substituted, preferably with at least one hydroxyl group, ii) a linear or branched $(C_2$-$C_{13})$alkenyl group which is optionally substituted, preferably with at least one hydroxyl group; the alkyl or alkenyl group particularly contain between 2 and 13 carbon atoms.

In particular, the odorous molecules are chosen from acetic acid, 2-propenoic acid, propanoic acid, 2-methylpropanoic acid, 2-methylpropenoic acid, 2-butenoic acid, 2-methyl-2-butenoic acid, 3-methyl-2-butenoic acid, butanoic acid, 2-methylbutanoic acid, 3-methylbutanoic acid, 3-hydroxybutanoic acid, 3-hydroxy-3-methylbutanoic acid, 2-pentenoic acid, 2-methyl-2-pentenoic acid, 3-methyl-2-pentenoic acid, pentanoic acid, 2-methylpentanoic acid, 3-methylpentanoic acid, 3-hydroxypentanoic acid, 3-hydroxy-3-methylpentanoic acid, 3-methyl-2-hexenoic acid, 3-hydroxy-3-methylhexanoic acid, 3-hydroxy-4-methyloctanoic acid, 3-hydroxyhexanoic acid, 2-heptenoic acid, 2-methyl-2-heptenoic acid, 3-methyl-2-heptenoic acid, heptanoic acid, 2-methylheptanoic acid, 3-methylheptanoic acid, 3-hydroxyheptanoic acid, 3-hydroxy-3-methylheptanoic acid, 2-octenoic acid, 2-methyl-2-octenoic acid, 3-methyl-2-octenoic acid, octanoic acid, 2-methyloctanoic acid, 3-methyloctanoic acid, 3-hydroxyoctanoic acid, 3-hydroxy-3-methyloctanoic acid, 2-nonenoic acid, 2-methyl-2-nonenoic acid, 3-methyl-2-nonenoic acid, nonanoic acid, 2-methylnonanoic acid, 3-methylnonanoic acid, 3-hydroxynonanoic acid, 3-hydroxy-3-methylnonanoic acid, 2-decenoic acid, 2-methyl-2-decenoic acid, 3-methyl-2-decenoic acid, decanoic acid, 2-methyldecanoic acid, 3-methyldecanoic acid, 3-hydroxydecanoic acid, 3-hydroxy-3-methyldecanoic acid, 10-hydroxydecanoic acid, 2-undecenoic acid, 2-methyl-2-undecenoic acid, 3-methyl-2-undecenoic acid, undecanoic acid, 2-methylundecanoic acid, 3-methylundecanoic acid, 3-hydroxyundecanoic acid, 3-hydroxy-3-methylundecanoic acid, dodecanoic acid, 2-hydroxydodecanoic acid, tridecanoic acid, 2-hydroxydodecanoic acid and tridecanoic acid.

In particular, the acid(s) are branched and/or substituted with at least one hydroxyl group.

More particularly, the odorous molecules are chosen from 2-methylpropanoic acid, 3-methyl-2-hexenoic acid, 3-hydroxy-3-methylhexanoic acid, 3-hydroxy-4-methyloctanoic acid, 3-hydroxyhexanoic acid and 3-hydroxyoctanoic acid.
b) Sulfanylalkanols or mercaptoalkanols such as those of formula (T2) below:

HS—$R^{12}$—OH  (T2)

in which formula (T2) $R^{12}$ represents a linear or branched ($C_1$-$C_{10}$) and preferably ($C_1$-$C_6$) alkylene group.

In particular, the odorous molecules are chosen from 3-methyl-3-sulfanylhexan-1-ol, 3-sulfanylhexan-1-ol, 2-methyl-3-sulfanylbutan-1-ol, 3-sulfanylpentan-1-ol, 3-sulfanylbutan-1-ol, 3-methyl-3-sulfanylpentan-1-ol and 3-methyl-3-sulfanylbutan-1-ol.

c) Steroids such as those of formula (T3) below:

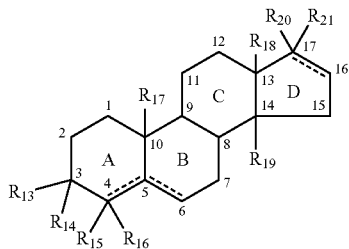

and also optical isomers thereof, cosmetic organic or mineral acid or base salts thereof, and solvates such as hydrates, in which formula (T3):
  $R_{13}$ and $R_{14}$, which may be identical or different, represent a hydrogen atom or a hydroxyl group, or alternatively $R_{13}$ and $R_{14}$ form, together with the carbon atom that bears them, an oxo group;
  $R_{15}$ and $R_{16}$, which may be identical or different, represent a hydrogen atom, a linear or branched ($C_1$-$C_8$)alkyl group, such as methyl, or a hydroxyl group, or alternatively $R_{15}$ and $R_{16}$ form, together with the carbon atom that bears them, an oxo group, in which case the bond between carbon atoms 4 and 5 is a single bond;
  ---- represents a single or a double bond, it being understood that when one of the two bonds between the two carbon atoms 4 and 5 or 5 and 6 is a double bond, then the other bond is a single bond;
  $R_{17}$, $R_{18}$ and $R_{19}$, which may be identical or different, represent a hydrogen atom or a linear or branched ($C_1$-$C_8$)alkyl group, such as methyl;
  $R_{20}$ and $R_{21}$, which may be identical or different, represent a hydrogen atom, a linear or branched ($C_1$-$C_8$)alkyl group, such as methyl, a hydroxyl group, a group —C($X^1$)—$X^2$—$R_{22}$, —$X^2$—C($X^1$)—$R_{22}$, —C($X^1$)—$R_{22}$, with $X^1$ and $X^2$ being as defined previously, preferably represents an oxygen atom, $R_{22}$ representing a hydrogen atom or a ($C_1$-$C_6$)alkyl group optionally substituted with a hydroxyl group, or alternatively $R_{20}$ and $R_{21}$ form, together with the carbon atom that bears them, an oxo group, in which case the bond between carbon atoms 16 and 17 is a single bond.

Mention may be made in particular of steroids chosen from androst-16-ene steroids, especially 5α-androst-16-en-3-one and 5α-androst-16-en-3α-ol, androst-2-en-17-one, androsta-4,16-dien-3-one, androsta-5,16-dien-3-ol, androst-4-en-3,17-dione, androstan-3-one, DHEA (dehydroepiandrosterone), testosterone, DHT (dehydrotestosterone) and 3-hydroxy-5-androstan-17-one.

d) Molecules chosen from amino acids such as those of formula (T4) below:

$R_{23}$-ALK-$R_{24}$  (T4)

in which formula (T4):
  $R_{23}$ and $R_{24}$, which may be identical or different, represent a —C($X^1$)—$X^2$—$R_{25}$, —$X^2$—C($X^1$)—$R_{25}$, —C($X^1$)—$R_{25}$, with $X^1$ and $X^2$ as defined previously, preferably $X^1$ represents an oxygen atom and $X^2$ represents an NH group; $R_{25}$ representing a hydrogen atom, a linear or branched ($C_1$-$C_8$)alkyl or linear or branched ($C_2$-$C_8$)alkenyl group, such as methyl, optionally substituted with a hydroxyl group;
  ALK represents a linear or branched ($C_1$-$C_8$)alkylene group, optionally substituted with a group —C($X^1$)—$X^2$—$R_{25}$, or —$X^2$—C($X^1$)—$R_{25}$, with $R_{25}$, $X^1$ and $X^2$ as defined previously, preferably ALK is a linear $C_2$-$C_4$ group such as a linear $C_3$ group, substituted with a carboxyl group.

In particular, mention may be made of the conjugated product of glutamine with 3-methyl-2-hexenoic acid and the conjugated product of glutamine with 3-hydroxy-3-methylhexanoic acid, N2-[3-methylhex-2-enoyl]glutamine, N2-[3-methyl-3-hydroxyhexanoyl]glutamine, N2-acetylglutamine, N2-[prop-2-enoyl]glutamine, N2-[2-methylprop-2-enoyl]glutamine, N2-propanoylglutamine, N2-[2-methylpropanoyl]glutamine, N2-[but-2-enoyl]glutamine, N2-[2-methylbut-2-enoyl]glutamine, N2-butanoylglutamine, N2-[2-methylbutanoyl]glutamine, N2-[3-methylbutanoyl]glutamine, N2-[3-hydroxybutanoyl]glutamine, N2-[3-hydroxy-3-methylbutanoyl]glutamine, N2-[pent-2-enoyl]glutamine, N2-[2-methylpent-2-enoyl]glutamine, N2-pentanoylglutamine, N2-[2-methylpentanoyl]glutamine, N2-[3-methylpentanoyl]glutamine, N2-[3-hydroxypentanoyl]glutamine, N2-[3-hydroxy-3-methylpentanoyl]glutamine, N2-[hex-2-enoyl]glutamine, N2-[2-methylhex-2-enoyl]glutamine, N2-hexanoylglutamine, N2-[2-methylhexanoyl]glutamine, N2-[3-methylhexanoyl]glutamine, N2-[3-hydroxyhexanoyl]glutamine, N2-[hept-2-enoyl]glutamine, N2-[2-methylhept-2-enoyl]glutamine, N2-heptanoylglutamine, N2-[2-methylheptanoyl]glutamine, N2-[3-methylheptanoyl]glutamine, N2-[3-hydroxyheptanoyl]glutamine, N2-[3-hydroxy-3-methylheptanoyl]glutamine, N2-[oct-2-enoyl]glutamine, N2-[2-methyloct-2-enoyl]glutamine, N2-octanoylglutamine, N2-[2-methyloctanoyl]glutamine, N2-[3-methyloctanoyl]glutamine, N2-[3-hydroxyoctanoyl]glutamine, N2-[3-hydroxy-3-methyloctanoyl]glutamine, N2-[non-2-enoyl]glutamine, N2-[2-methylnon-2-enoyl]glutamine, N2-nonanoylglutamine, N2-[2-methylnonanoyl]glutamine, N2-[3-methylnonanoyl]glutamine, N2-[3-hydroxynonanoyl]glutamine, N2-[3-hydroxy-3-methylnonanoyl]glutamine, N2-[dec-2-enoyl]glutamine, N2-[2-methyldec-2-enoyl]glutamine, N2-decanoylglutamine, N2-[2-methyldecanoyl]glutamine, N2-[3-methyldecanoyl]glutamine, N2-[3-hydroxydecanoyl]glutamine, N2-[3-hydroxy-3-methyldecanoyl]glutamine, N2-[undec-2-enoyl] glutamine, N2-[2-methylundec-2-enoyl]glutamine, N2-undecanoylglutamine, N2-[2-methylundecanoyl]glutamine, N2-[3-methylundecanoyl]glutamine, N2-[3-hydroxyundecanoyl]glutamine, N2-[3-hydroxy-3-methylundecanoyl]glutamine, N2-[dodec-2-enoyl]glutamine, N2-[2-methyldodec-2-enoyl]glutamine, N2-dodecanoylglutamine, N2-[2-methyldodecanoyl]glutamine, N2-[3-methyldodecanoyl]glutamine, N2-[3-hydroxydodecanoyl]glutamine, N2-[3-hydroxy-3-methyldodecanoyl]glutamine and Nα-hexanoylglutamine.

In particular, mention may be made of the conjugated product of glutamic acid with 3-methyl-2-hexenoic acid and the conjugated product of glutamic acid with 3-hydroxy-3-methylhexanoic acid, N2-[3-methylhex-2-enoyl]glutamic acid, N2-[3-methyl-3-hydroxyhexanoyl]glutamic acid, N2-acetylglutamic acid, N2-[prop-2-enoyl]glutamic acid, N2-[2-methylprop-2-enoyl]glutamic acid, N2-propanoylglutamic acid, N2-[2-methylpropanoyl]glutamic acid, N2-[but-2-enoyl]glutamic acid, N2-[2-methylbut-2-enoyl]glutamic acid, N2-butanoylglutamic acid, N2-[2-methylbutanoyl]glutamic acid, N2-[3-methylbutanoyl]glutamic acid, N2-[3-hydroxybutanoyl] glutamic acid, N2-[3-hydroxy-3-methylbutanoyl] glutamic acid, N2-[pent-2-enoyl]glutamic acid, N2-[2-methylpent-2-enoyl]glutamic acid, N2-pentanoylglutamic acid, N2-[2-methylpentanoyl]glutamic acid, N2-[3-methylpentanoyl]glutamic acid, N2-[3-hydroxypentanoyl]glutamic acid, N2-[3-hydroxy-3-methylpentanoyl]glutamic acid, N2-[hex-2-enoyl]glutamic acid, N2-[2-methylhex-2-enoyl]glutamic acid, N2-hexanoylglutamic acid, N2-[2-methylhexanoyl]glutamic acid, N2-[3-methylhexanoyl]glutamic acid, N2-[3-hydroxyhexanoyl] glutamic acid, N2-[hept-2-enoyl]glutamic acid, N2-[2-methylhept-2-enoyl]glutamic acid, N2-heptanoylglutamic acid, N2-[2-methylheptanoyl]glutamic acid, N2-[3-methylheptanoyl]glutamic acid, N2-[3-hydroxyheptanoyl]glutamic acid, N2-[3-hydroxy-3-methylheptanoyl]glutamic acid, N2-[oct-2-enoyl]glutamic acid, N2-[2-methyloct-2-enoyl]glutamic acid, N2-octanoylglutamic acid, N2-[2-methyloctanoyl]glutamic acid, N2-[3-methyloctanoyl]glutamic acid, N2-[3-hydroxyoctanoyl] glutamic acid, N2-[3-hydroxy-3-methyloctanoyl] glutamic acid, N2-[non-2-enoyl]glutamic acid, N2-[2-methylnon-2-enoyl]glutamic acid, N2-nonanoylglutamic acid, N2-[2-methylnonanoyl] glutamic acid, N2-[3-methylnonanoyl]glutamic acid, N2-[3-hydroxynonanoyl]glutamic acid, N2-[3-hydroxy-3-methylnonanoyl]glutamic acid, N2-[dec-2-enoyl]glutamic acid, N2-[2-methyldec-2-enoyl]glutamic acid, N2-decanoylglutamic acid, N2-[2-methyldecanoyl]glutamic acid, N2-[3-methyldecanoyl]glutamic acid, N2-[3-hydroxydecanoyl]glutamic acid, N2-[3-hydroxy-3-methyldecanoyl]glutamic acid, N2-[undec-2-enoyl] glutamic acid, N2-[2-methylundec-2-enoyl]glutamic acid, N2-undecanoylglutamic acid, N2-[2-methylundecanoyl]glutamic acid, N2-[3-methylundecanoyl] glutamic acid, N2-[3-hydroxyundecanoyl]glutamic acid, N2-[3-hydroxy-3-methylundecanoyl]glutamic acid, N2-[dodec-2-enoyl]glutamic acid, N2-[2-methyldodec-2-enoyl]glutamic acid, N2-dodecanoylglutamic acid, N2-[2-methyldodecanoyl]glutamic acid, N2-[3-methyldodecanoyl]glutamic acid, N2-[3-hydroxydodecanoyl]glutamic acid, N2-[3-hydroxy-3-methyldodecanoyl]glutamic acid and Nα-hexanoylglutamic acid.

e) Acid esters such as the acid esters of formula (T1) as defined previously, preferentially the esters of formula (T'1) below:

$$R^{11}-C(O)-OR'^{11} \quad (T'1)$$

in which formula (T'1):
R$^{11}$ is as defined previously; and
R'$^{11}$ represents i) a linear or branched (C$_1$-C$_{20}$)alkyl group which is optionally substituted, preferably with at least one hydroxyl group, ii) a linear or branched (C$_2$-C$_{20}$)alkenyl group which is optionally substituted, preferably with at least one hydroxyl group; the alkyl or alkenyl group particularly contain between 2 and 14 carbon atoms, and more particularly R'$^{11}$ represents a linear or branched (C$_1$-C$_6$) alkyl group such as methyl.

In particular, the methyl esters of the following acids are chosen: acetic acid, 2-propenoic acid, propanoic acid, 2-methylpropanoic acid, 2-methylpropenoic acid, 2-butenoic acid, 2-methyl-2-butenoic acid, 3-methyl-2-butenoic acid, butanoic acid, 2-methylbutanoic acid, 3-methylbutanoic acid, 3-hydroxybutanoic acid, 3-hydroxy-3-methylbutanoic acid, 2-pentenoic acid, 2-methyl-2-pentenoic acid, 3-methyl-2-pentenoic acid, pentanoic acid, 2-methylpentanoic acid, 3-methylpentanoic acid, 3-hydroxypentanoic acid, 3-hydroxy-3-methylpentanoic acid, 3-methyl-2-hexenoic acid, 3-hydroxy-3-methylhexanoic acid, 3-hydroxy-4-methyloctanoic acid, 3-hydroxyhexanoic acid, 2-heptenoic acid, 2-methyl-2-heptenoic acid, 3-methyl-2-heptenoic acid, heptanoic acid, 2-methylheptanoic acid, 3-methylheptanoic acid, 3-hydroxyheptanoic acid, 3-hydroxy-3-methylheptanoic acid, 2-octenoic acid, 2-methyl-2-octenoic acid, 3-methyl-2-octenoic acid, octanoic acid, 2-methyloctanoic acid, 3-methyloctanoic acid, 3-hydroxyoctanoic acid, 3-hydroxy-3-methyloctanoic acid, 2-nonenoic acid, 2-methyl-2-nonenoic acid, 3-methyl-2-nonenoic acid, nonanoic acid, 2-methylnonanoic acid, 3-methylnonanoic acid, 3-hydroxynonanoic acid, 3-hydroxy-3-methylnonanoic acid, 2-decenoic acid, 2-methyl-2-decenoic acid, 3-methyl-2-decenoic acid, decanoic acid, 2-methyldecanoic acid, 3-methyldecanoic acid, 3-hydroxydecanoic acid, 3-hydroxy-3-methyldecanoic acid, 10-hydroxydecanoic acid, 2-undecenoic acid, 2-methyl-2-undecenoic acid, 3-methyl-2-undecenoic acid, undecanoic acid, 2-methylundecanoic acid, 3-methylundecanoic acid, 3-hydroxyundecanoic acid, 3-hydroxy-3-methylundecanoic acid, dodecanoic acid, 2-hydroxydodecanoic acid, tridecanoic acid, 2-hydroxydodecanoic acid or tridecanoic acid.

f) The conjugated products of 3-methyl-3-sulfanylhexan-1-ol in particular of formula (T'4) below:

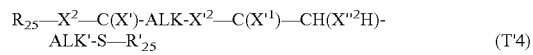

$$R_{25}-X^2-C(X')-ALK-X'^2-C(X^1)-CH(X''^2H)-ALK-S-R'_{25} \quad (T'4)$$

in which formula (T'4):
R$_{25}$ and R'$_{25}$, which may be identical or different, represent a hydrogen atom, a linear or branched (C$_1$-C$_5$)alkyl or linear or branched (C$_2$-C$_8$)alkenyl group, such as methyl, optionally substituted with a hydroxyl group; preferably, R$_{25}$ represents a hydrogen atom and R'$_{25}$ represents a (C$_1$-C$_6$)alkyl group optionally substituted with a hydroxyl group;

ALK and ALK', which may be identical or different, represent a linear or branched ($C_1$-$C_5$)alkylene group optionally substituted with a group —$X^2$—$R_{25}$, with $R_{25}$;

$X^1$ and $X^2$, which may be identical or different, are as defined previously, preferably $X^1=X^2=O$;

$X'^2$ and $X'^2$, and $X''^2$, which may be identical or different, are as defined for $X^1$ and $X^2$ respectively, preferably $X'^2=X''^2=NH$ and/or $X'^1=O$.

In particular, the odorous compounds are chosen from the following compounds: S-(1-hydroxy-3-methylhexan-3-yl)cysteinylglycine, S-(1-hydroxy-2-methylhexan-3-yl)cysteinylglycine, S-(1-hydroxy-2-methylbutan-3-yl)cysteinylglycine, S-(1-hydroxypentan-3-yl)cysteinylglycine, S-(1-hydroxybutan-3-yl)cysteinylglycine, S-(1-hydroxy-3-methylpentan-3-yl)cysteinylglycine, S-(1-hydroxy-3-methylbutan-3-yl)cysteinylglycine, S-(1-hydroxyhexan-3-yl)cysteinylglycine and S-(1-hydroxy-2-methylhexan-3-yl)cysteinylglycine, and also the enantiomers and racemic mixtures thereof.

g) Sulfo-conjugated steroids, in particular the sulfate derivatives of formula (T3) as defined previously, which comprise at least one sulfate function.

In particular, the odorous compounds are chosen from the sulfates derived from dehydroepiandrosterone (DHEA), androsterone and testosterone, 5α-androst-16-en-3α-sulfate, androsta-5,16-dien-3β-sulfate, dehydroepiandrosterone sulfate, testosterone sulfate, 5α-dehydrotestosterone sulfate and 5α-androstan-17-on-3α-sulfate.

In particular, mention may be made of the odorous compounds of formula (T'1) chosen from the methyl ester of 3-hydroxy-3-methylhexanoic acid, the methyl ester of 3-hydroxy-4-methyloctanoic acid, the methyl ester of (E)-3-methyl-2-hexenoic acid, the methyl ester of 3-hydroxyhexanoic acid and the methyl ester of 3-hydroxyoctanoic acid.

More particularly, the methyl esters of the following acids: 2-methylpropanoic acid, 3-methyl-2-hexenoic acid, 3-hydroxy-3-methylhexanoic acid, 3-hydroxy-4-methyloctanoic acid, 3-hydroxyhexanoic acid and 3-hydroxyoctanoic acid.

Preferably, the imprint molecule(s) are of formulae (T1) and (T4) and in particular 3-methyl-2-hexenoic acid and N-[3-methylhex-2-enoyl]glutamic acid.

The Porogenic Solvent

The MIPs are prepared from porogenic solvent, the polarity of which preferably i) makes it possible to dissolve the imprint molecule and/or ii) is suited to the interaction of the said imprint molecule with the functional monomers.

The term "porogenic" solvent means a solvent that is capable of creating a porous network capable of conveying the templates or odorous molecules or the molecules that are the source of the unpleasant odour to the imprints in the formed polymer.

According to a particular embodiment of the invention, the volume of porogenic solvent used for the preparation of a "bulk" polymer as defined previously is calculated by means of the following relationship $n=V_{porogenic\ solvent}/(V_{porogenic\ solvent}+V_{functional\ monomer})$, with n inclusively between 0.2 and 0.9, more particularly between 0.3 and 0.8 and preferentially between 0.5 and 0.6.

According to a preferred mode of the invention, when hydrogen bonds or ionic interactions or coordination bonds with transition metals are involved, the porogenic solvents in the process for synthesizing the MIP(s) of the invention are solvents of weak hydrogen-bond donating or accepting nature, and which are sparingly polar, of the type such as benzene, toluene, chloroform or dichloromethane.

According to a preferred mode, when the dissolution of the imprint molecule in the prepolymerization mixture demands it, the porogenic solvent is a polar protic solvent such as $C_1$-$C_8$ alcohols, for instance ethanol.

According to another preferred embodiment, the porogenic solvent is a polar aprotic solvent such as acetonitrile, tetrahydrofuran (THF), dialkylformamides (dimethylformamide and diethylformamide), N-methyl-2-pyrrolidinone (NMP), N-ethyl-2-pyrrolidinone (NEP), N,N'-dimethylpropyleneurea (DMPU) and dimethyl sulfoxide (DMSO).

According to a particularly advantageous mode, the composition of the invention comprising the MIP(s) also comprises at least one cosmetic porogenic solvent used during the synthesis of the said MIP(s) with the imprint molecule(s).

Advantageously, the porogenic solvent may be supplemented with a modifier of hydrogen-bond donor or acceptor nature, which is acidic, rather organic acids, in particular ($C_1$-$C_5$)carboxylic acids such as acetic acid; and/or which is basic, rather organic bases of the (di)($C_1$-$C_8$)alkylamine type such as diethylamine.

Preferentially, the porogenic solvent used in the invention for preparing the MIPs is a solvent chosen from polar protic solvents such as $C_1$-$C_8$ alcohols, for instance ethanol.

Characterization of the MIP

The characterization of the MIP consists in demonstrating the formation of imprints and in evaluating their number and their affinity for the targeted molecule. These results may be complemented by a study of the morphology of the material (size and shape of the particles, porosity and specific surface area). These methods are known to those skilled in the art (see for example point 1.7, p 49 of the June 2010 doctoral thesis by R. Walsh, *Development and characterization of MIP* repository.wit.ie/1619/1/Development_and_characterisation_of_molecularly_imprinted_suspension_polymers.pdf)

Cosmetic Compositions:

The cosmetic composition according to the invention is a composition which is in a physiologically acceptable medium, which is preferentially a dermatologically acceptable medium, i.e. a medium which has no odour or unpleasant aspect, and which is perfectly compatible with the topical administration route.

In the present case, where the composition is intended for topical administration, that is to say for administration by application at the surface of the keratin material under consideration, such a medium is considered in particular to be physiologically acceptable when it does not cause stinging, tightness or redness unacceptable to the user.

A physiologically acceptable medium is preferentially a cosmetically or dermatologically acceptable medium, that is to say a medium which is devoid of unpleasant odour or appearance and which is entirely compatible with the topical administration route.

In the present case, where the composition is intended for topical administration, that is to say for administration by application at the surface of the keratin material under consideration, such a medium is considered in particular to be physiologically acceptable when it does not cause stinging, tightness or redness unacceptable to the user.

The cosmetic composition according to the invention may be water or a mixture of water and of one or more organic solvents or a mixture of organic solvents.

The term "organic solvent" means an organic substance that is capable of dissolving or dispersing another substance without chemically modifying it.

The deodorant cosmetic composition may also comprise, besides the MIPs in accordance with the invention, at least one additional deodorant active agent and/or at least one antiperspirant active agent as defined below.

Deodorant Active Agents

According to a particular embodiment of the invention, the composition according to the invention contains one or more deodorant active agents, for instance:

bacteriostatic agents or other bactericidal agents, such as 2,4,4'-trichloro-2'-hydroxydiphenyl ether (triclosan), 2,4-dichloro-2'-hydroxydiphenyl ether, 3',4',5'-trichlorosalicylanilide, 1-(3',4'-dichlorophenyl)-3-(4'-chlorophenyl)urea (triclocarban) or 3,7,11-trimethyldodeca-2,5,10-trienol (farnesol); quaternary ammonium salts, such as cetyltrimethylammonium salts or cetylpyridinium salts; chlorhexidine and its salts; diglyceryl monocaprate, diglyceryl monolaurate, glyceryl monolaurate; polyhexamethylene biguanide salts;

zinc salts;

odour absorbers such as zeolites, cyclodextrins, metal oxide silicates such as those described in patent application US 2005/063 928; metal oxide particles modified with a transition metal, as described in patent applications US 2005/084 464 and US 2005/084 474, aluminosilicates such as those described in patent application EP 1 658 863, chitosan-based particles such as those described in patent U.S. Pat. No. 6,916,465;

substances which block the enzymatic reactions responsible for the formation of odorous compounds, such as arylsulfatase, 5-lipoxygenase, aminocylase or β-glucuronidase inhibitors;

and mixtures thereof.

The deodorant active agents can be present in the composition according to the invention in a proportion of from 0.01% to 10% by weight and preferably in a proportion of from 0.1% to 5% by weight, with respect to the total weight of the composition.

Antiperspirant Active Agents

The antiperspirant active agents are preferably chosen from aluminium and/or zirconium salts; complexes of zirconium hydroxychloride and of aluminium hydroxychloride with an amino acid, such as those described in patent U.S. Pat. No. 3,792,068, commonly known as "ZAG" complexes. Such complexes are generally known under the name ZAG (when the amino acid is glycine). Mention may be made, among these products, of aluminium zirconium octachlorohydrex GLY, aluminium zirconium pentachlorohydrex GLY, aluminium zirconium tetrachlorohydrate GLY and aluminium zirconium trichlorohydrate GLY.

Use will more particularly be made of aluminium chlorohydrate in the activated or non-activated form.

The antiperspirant active agents can be present in the composition according to the invention in a proportion of from 0.001% to 30% by weight and preferably in a proportion of from 0.5% to 25% by weight, with respect to the total weight of the composition.

Galenical Forms

The composition according to the invention can be provided in any formulation form conventionally used for a topical application and in particular in the form of aqueous gels or of aqueous or aqueous/alcoholic solutions. They can also, by addition of a fatty or oily phase, be provided in the form of dispersions of the lotion type, of emulsions with a liquid or semi-liquid consistency of the milk type, obtained by dispersion of a fatty phase in an aqueous phase (O/W) or vice versa (W/O), or of suspensions or emulsions with a soft, semi-solid or solid consistency of the cream or gel type, or alternatively of multiple emulsions (W/O/W or O/W/O), of microemulsions, of vesicular dispersions of ionic and/or nonionic type, or of wax/aqueous phase dispersions. These compositions are prepared according to the usual methods.

The compositions according to the invention may especially be conditioned in pressurized form in an aerosol device or in a pump-dispenser bottle; conditioned in a device equipped with a perforated wall, especially a grate; conditioned in a device equipped with a ball applicator ("roll-on"); conditioned in the form of wands (sticks) or in the form of a loose or compacted powder. In this regard, they comprise the ingredients generally used in products of this type, which are well known to a person skilled in the art.

According to another specific form of the invention, the compositions according to the invention can be anhydrous.

The term "anhydrous composition" means a composition containing less than 2% by weight of water, or even less than 0.5% of water, relative to the total weight of the composition, and especially free of water, the water not being added during the preparation of the composition but corresponding to the residual water provided by the mixed ingredients.

According to another specific form of the invention, the compositions according to the invention can be solid, in particular in the wand or stick form.

The term "solid composition" is intended to denote a composition for which the maximum force measured by texturometry during the penetration of a probe into the sample of formula is at least equal to 0.25 newtons, in particular at least equal to 0.30 newtons and especially at least equal to 0.35 newtons, assessed under precise measuring conditions as follows.

The formulae are poured hot into jars with a diameter of 4 cm and a depth of 3 cm. Cooling is carried out at ambient temperature. The hardness of the formulae produced is measured after an interval of 24 hours. The jars containing the samples are characterized in texturometry using a texture analyzer, such as that sold by Rheo, TA-XT2, according to the following protocol: a probe of stainless-steel ball type with a diameter of 5 mm is brought into contact with the sample at a rate of 1 mm/s. The measurement system detects the interface with the sample, with a detection threshold equal to 0.005 newton. The probe sinks 0.3 mm into the sample, at a rate of 0.1 mm/s. The measuring device records the change in the force measured in compression over time, during the penetration phase. The hardness of the sample corresponds to the mean of the maximum values of the force detected during the penetration, over at least three measurements.

Aqueous Phase

The compositions according to the invention intended for cosmetic use can comprise at least one aqueous phase. They are especially formulated as aqueous lotions or as water-in-oil or oil-in-water emulsions or as multiple emulsions (oil-in-water-in-oil or water-in-oil-in-water triple emulsions (such emulsions are known and described, for example, by C. Fox in "Cosmetics and Toiletries"—November 1986—Vol. 101—pages 101-112)).

The aqueous phase of the said compositions contains water and generally other water-soluble or water-miscible solvents. The water-soluble or water-miscible solvents comprise monoalcohols with a short chain, for example of $C_1$-$C_4$, such as ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol, glycerol and 1,3-propanediol will be used more particularly.

pH of the Composition

The composition according to the invention preferably has a pH ranging from 3 to 9, according to the support chosen.

According to a particular mode of the invention, the pH of the composition(s) is neutral or even slightly acidic. Preferably, the pH of the composition is between 6 and 7.

The pH of these compositions may be adjusted to the desired value by means of acidifying or basifying agents usually used in cosmetics, or alternatively using standard buffer systems.

The term "basifying agent" or "base" means an agent for increasing the pH of the composition in which it is present. The basifying agent is a Brønsted, Lowry or Lewis base. It may be mineral or organic. In particular, the said agent is chosen from a) aqueous ammonia, b) (bi)carbonate, c) alkanolamines such as monoethanolamine, diethanolamine, triethanolamine and derivatives thereof, d) oxyethylenated and/or oxypropylenated ethylenediamines, e) organic amines, f) mineral or organic hydroxides, g) alkali metal silicates such as sodium metasilicates, h) amino acids, preferably basic amino acids such as arginine, lysine, ornithine, citrulline and histidine, and i) the compounds of formula (III) below:

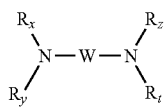

in which formula (III):

W is a divalent $C_1$-$C_6$ alkylene radical optionally substituted with one or more hydroxyl groups or a $C_1$-$C_6$ alkyl radical, and/or optionally interrupted with one or more heteroatoms such as oxygen or $NR_u$;

$R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (III) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Among the mineral or organic hydroxides, mention may be made of those chosen from a) hydroxides of an alkali metal, b) hydroxides of an alkaline-earth metal, for instance sodium hydroxide or potassium hydroxide, c) hydroxides of a transition metal, d) hydroxides of lanthanides or actinides, quaternary ammonium hydroxides and guanidinium hydroxide. The mineral or organic hydroxides a) and b) are preferred.

Among the acidifying agents for the compositions used in the invention, examples that may be mentioned include inorganic or organic acids, for instance hydrochloric acid, orthophosphoric acid, sulfuric acid, carboxylic acids, for instance acetic acid, tartaric acid, citric acid or lactic acid, or sulfonic acids.

The basifying agents and the acidifying agents as defined previously preferably represent from 0.001% to 20% by weight relative to the weight of the composition containing them and more particularly from 0.005% to 8% by weight of the composition.

Excipients:

The composition may also comprise one or more additional ingredients. It is understood that the amount of these ingredients may be adjusted by a person skilled in the art so as not to harm the desired effect in the context of the present invention. Among these ingredients, mention may be made of emulsifiers, fatty phases, oils, structuring agents, waxes, pasty compounds other than waxes, gelling agents (organic lipophilic gelling agents), thickeners, suspension agents, propellants and additives. Among these, mention may be made more particularly of:

Oil-in-Water Emulsifiers

The composition according to the invention may comprise at least one emulsifier. As emulsifiers that may be used in the oil-in-water emulsions or oil-in-water-in-oil triple emulsions, examples that may be mentioned include nonionic emulsifiers such as oxyalkylenated fatty acid esters of glycerol; oxyalkylenated fatty alkyl ethers; sugar esters such as sucrose stearate; and mixtures thereof.

Water-in-Oil Emulsifiers

Among the emulsifiers that may be used in the water-in-oil emulsions or water-in-oil-in-water-in-oil triple emulsions, examples that may be mentioned include alkyl dimethicone copolyols.

Mention will also be made, among the water-in-oil emulsifiers, of nonionic emulsifiers derived from fatty acids and polyols, alkyl polyglycosides (APGs), sugar esters and their mixtures.

The total amount of emulsifiers in the composition will preferably be, in the composition according to the invention, at active material contents ranging from 1% to 8% by weight and more particularly from 2% to 6% by weight, with respect to the total weight of the composition.

Fatty Phase

The compositions according to the invention can comprise at least one water-immiscible organic liquid phase, known as fatty phase. This phase generally comprises one or more hydrophobic compounds which render the said phase water-immiscible. The said phase is liquid (in the absence of structuring agent) at room temperature (20-25° C.). Preferentially, the water-immiscible organic-liquid organic phase in accordance with the invention generally comprises at least one volatile oil and/or non-volatile oil and optionally at least one structuring agent.

Oil(s)

The term "oil" means a fatty substance that is liquid at room temperature (25° C.) and atmospheric pressure (760 mmHg, i.e. $10^5$ Pa). The oil may be volatile or non-volatile.

For the purposes of the invention, the term "volatile oil" means an oil that is capable of evaporating on contact with the skin or the keratin fibre in less than one hour, at room temperature and atmospheric pressure. The volatile oils of the invention are volatile cosmetic oils which are liquid at ambient temperature and which have a non-zero vapour pressure, at ambient temperature and atmospheric pressure, ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

The oil can be chosen from any physiologically acceptable oil and in particular cosmetically acceptable oils, in particular mineral, animal, vegetable or synthetic oils; in particular volatile or non-volatile hydrocarbon-based oils and/or silicone oils and/or fluoro oils, and mixtures thereof.

More precisely, the term "hydrocarbon-based oil" means an oil mainly comprising carbon and hydrogen atoms and optionally one or more functions chosen from hydroxyl, ester, ether and carboxylic functions. Generally, the oil exhibits a viscosity of 0.5 to 100 000 mPa·s, preferably of 50 to 50 000 mPa·s and more preferably of 100 to 30 000 mPa·s.

Structuring Agent(s)

The compositions according to the invention comprising a fatty phase can additionally comprise at least one structuring agent for the said fatty phase, which can preferably be chosen from waxes, pasty compounds, inorganic or organic lipophilic gelling agents, and their mixtures.

Wax(es)

The wax is generally a lipophilic compound which is solid at ambient temperature (25° C.), which exhibits a reversible solid/liquid change in state and which has a melting point of greater than or equal to 30° C. which can range up to 200° C. and in particular up to 120° C.

In particular, the waxes suitable for the invention can exhibit a melting point of greater than or equal to 45° C. and in particular of greater than or equal to 55° C.

The composition according to the invention will preferably comprise a content of wax(es) ranging from 3% to 20% by weight relative to the total weight of the composition, in particular from 5% to 15% and more particularly from 6% to 15%.

According to one particular form of the invention, in the context of anhydrous solid compositions in stick form, use will be made of polyethylene microwaxes in the form of crystallites with an aspect ratio at least equal to 2, and with a melting point ranging from 70 to 110° C. and preferably from 70 to 100° C., so as to reduce or even eliminate the presence of strata in the solid composition. These crystallites in needle form and in particular their dimensions can be characterized visually according to the following method.

Pasty Compound(s)

For the purposes of the present invention, the term "pasty compound" means a lipophilic fatty compound that undergoes a reversible solid/liquid change of state, having in the solid state an anisotropic crystal organization, and comprising, at a temperature of 23° C., a liquid fraction and a solid fraction.

Organic Lipophilic Gelling Agents

The polymeric organic lipophilic gelling agents are, for example, partially or totally crosslinked elastomeric organopolysiloxanes, of three-dimensional structure, such as those sold under the names.

Additives

The cosmetic compositions according to the invention may also comprise cosmetic adjuvants chosen from softeners, antioxidants, opacifiers, stabilizers, moisturizers, vitamins, bactericides, preserving agents, polymers, fragrances, organic powders or any other ingredient usually used in cosmetics for this type of application.

Thickeners and Suspending Agents

The compositions according to the invention may also comprise at least one thickener and/or at least one suspending agent.

Thickeners

The thickeners may be chosen from carboxyvinyl polymers; polyacrylamides; 2-acrylamido-2-methylpropanesulfonic acid polymers and copolymers, which are optionally crosslinked and/or neutralized; copolymers of 2-acrylamido-2-methylpropanesulfonic acid and of hydroxyethyl acrylate; cellulose derivatives; polysaccharides; silicas, and also cationic polymers.

Suspending Agents

The composition of the invention may also comprise one or more suspending agents, which are preferably chosen from hydrophobic modified montmorillonite clays such as hydrophobic modified bentonites or hectorites.

The suspending agents are preferably present in amounts ranging from 0.1% to 5% by weight and more preferentially from 0.2% to 2% by weight, relative to the total weight of the composition.

The amounts of these various constituents which can be present in the cosmetic composition according to the invention are those conventionally used in compositions for the treatment of perspiration.

Aerosols

The compositions according to the invention can also be pressurized and be packaged in an aerosol device made up of:

(A) a container comprising a composition as defined previously, (B) at least one propellant and one means for dispensing the said aerosol composition.

Process for Using the MIPs as Deodorant Agents

One particular embodiment of the invention relates to processes for trapping odours.

According to a particular mode of the invention, the trapping process is performed using a cosmetic composition in solution, powder, mousse, etc. form, which is deposited on the surface of the skin especially on parts with a high density of sweat glands such as the armpits.

One particular mode of the invention concerns a trapping process which is performed at skin temperature.

The examples that follow serve to illustrate the invention without, however, being limiting in nature.

EXAMPLES

Example 1

Synthesis of MIP1 and Trapping Test

Synthesis of MIP1

| Ingredients | | Amount | Mole ratio as a function of the imprint molecule or template |
|---|---|---|---|
| 3-Methyl-2-hexenoic acid (3M2H) | Template molecule | 270 mg | 1 |
| 3-Aminopropyltriethoxysilane (APTES) | Functional monomer | 500 mg | 1 |
| Tetraethyl orthosilicate (TEOS) | Crosslinking agent | 10 g | 24 |
| Aqueous ammonia (28% aqueous solution) | Polymerization initiator | 3 ml | |
| Ethanol | Solvent (porogen) | 2*50 ml | |

3M2H, APTES and TEOS are mixed together in the proportions and amounts defined in the above table. Ethanol (50 ml) is added and the mixture is stirred for 5 minutes. Next, the aqueous ammonia is added (dropwise). At the end of the addition, ethanol (50 ml) is added. The mixture is stirred for 18 hours at room temperature and at atmospheric pressure, filtered, washed with ethanol (100 ml), with acetone (100 ml) and then air-dried. The crude white powder is then triturated in the presence of a solution derived from a mixture of acetic acid (4 ml) and ethanol (100 ml), for 15 minutes. The said powder is finally filtered off, washed with ethanol (100 ml) and then air-dried. A white powder is obtained.

The morphology of the particles is characterized using an optical microscopy machine (Morphologi G3 from the company Malvern Instruments). 2 mg of the powder are sonicated in 1 mL of water for 5 minutes and then analysed. The particles have a mean diameter of 1.92 microns and a mean circularity of 0.74.

Synthesis of the Comparative NIP1:

NIP1 is synthesized under the same operating conditions and using the same amounts of ingredients as for MIP1, except that the mixture does not comprise any template. A white powder is obtained (4.5 g).

The morphology of the particles is characterized as in example MIP1. The particles have a mean diameter of 2.53 microns and a mean circularity of 0.76.

Example 2

Synthesis of MIP2

Synthesis of MIP2

| Ingredients | | Amount | Mole ratio as a function of the imprint molecule or template |
|---|---|---|---|
| N-[3-Methylhex-2-enoyl]glutamic acid (glum3M2H) | Template molecule | 1.1 g | 1 |
| 3-Aminopropyltriethoxysilane (APTES) | Functional monomer | 1 g | 1 |
| Tetraethyl orthosilicate (TEOS) | Crosslinking agent | 10 g | 10 |
| Aqueous ammonia (28% aqueous solution) | Polymerization initiator | 3 ml | |
| Ethanol | Solvent (porogen) | 100 ml | |

Glum3M2H, APTES and TEOS are mixed together in the proportions and amounts defined in the above table. Ethanol (100 ml) is added and the mixture is stirred for 5 minutes. A solution of hydrochloric acid (37%, 0.5 ml) in water (50 ml) is added and the mixture is stirred for 15 minutes. Next, the aqueous ammonia is added (dropwise). The mixture is stirred for 18 hours at room temperature and at atmospheric pressure, filtered, washed with ethanol (100 ml) and with acetone (100 ml), and then air-dried. The white powder is triturated with a solution of acetic acid (4 ml) and ethanol (100 ml), for 15 minutes, and then filtered off, washed with ethanol (100 ml) and then air-dried. A white powder is obtained (3.7 g). The morphology of the particles is characterized as in Example MIP1. The particles have a mean diameter of 1.15 microns and a mean circularity of 0.88.

Synthesis of the Comparative NIP2:

NIP2 is synthesized under the same operating conditions and amount as for MIP2, the only difference being that the mixture does not comprise the template. A white powder is obtained (4.1 g).

The morphology of the particles is characterized as in example MIP1. The particles have a mean diameter of 1.16 microns and a mean circularity of 0.53.

Sensory Odour Tests 100 mg of the MIPs or NIPs are placed in bottles containing an ethanolic solution of the odorous molecule 3M2H (1.5 g %; 5 ml). The bottles are closed and left for 3 hours. Next, the bottles are opened just before performing the sensory test. The bottles are independently held a distance of 2 cm from the nose for 3 seconds. The intensity of the odour is judged by comparing a control bottle containing ethanol (5 ml) and a bottle containing an ethanolic solution of the odorous molecule 3M2H (1.5 g %; 5 ml). A strong odour intensity equivalent to the odour of the bottle containing an ethanolic solution of the odorous molecule (1.5 g %; 5 ml) is given a score of 10. A weak odour intensity equivalent to the odour of the bottle containing ethanol alone is given a score of 1.

Results

| Sample | Odour intensity (1 to 10) |
|---|---|
| MIP1 | 2 |
| NIP1 | 7 |
| MIP2 | 5 |
| NIP2 | 8 |

In all these examples, the MIPs very significantly reduce the odour intensity compared with the NIPs. The reduction of the odour intensity demonstrates that the MIPs have a much better capacity for trapping the odorous molecules than the NIPs.

The invention claimed is:

1. A cosmetic composition for reducing body odor, the composition comprising:
   a physiologically acceptable medium chosen from water, organic solvents, or mixtures thereof,
   at least one molecularly imprinted polymer configured to trap at least one molecule at the surface of keratin materials in order to reduce body odor, and
   at least one additional agent for reducing body odor chosen from at least one antiperspirant active agent or at least one deodorant active agent other than the at least one molecularly imprinted polymer,
   wherein the at least one molecularly imprinted polymer is obtained by:
   A) sol-gel polymerization of a mixture comprising:
      i) at least one functional silane monomer;
      ii) at least one crosslinking agent;
      iii) at least one porogenic solvent;
      iv) at least one template molecule chosen from:
         linear or branched, saturated or unsaturated, and/or optionally substituted C2-C13 aliphatic acids chosen from acetic acid, 2-propenoic acid, propanoic acid, 2-methylpropanoic acid, 2-methylpropenoic acid, 2-butenoic acid, 2-methyl-2-butenoic acid, 3-methyl-2-butenoic acid, butanoic acid, 2-methylbutanoic acid, 3-methylbutanoic acid, 3-hydroxybutanoic acid, 3-hydroxy-3-methylbutanoic acid, 2-pentenoic acid, 2-methyl-2-pentenoic acid, 3-methyl-2-pentenoic acid, pentanoic acid, 2-methylpentanoic acid, 3-methylpentanoic acid, 3-hydroxypentanoic acid, 3-hydroxy-3-methylpentanoic acid, 3-methyl-2-hexenoic acid, 3-hydroxy-3-methylhexanoic acid, 3-hydroxy-4-methyloctanoic acid, 3-hydroxyhexanoic acid, 2-heptenoic acid, 2-methyl-2-heptenoic acid, 3-methyl-2-heptenoic acid, heptanoic acid, 2-methylheptanoic acid, 3-methylheptanoic acid, 3-hydroxyheptanoic acid, 3-hydroxy-3-methylheptanoic acid, 2-octenoic acid, 2-methyl-2-octenoic acid, 3-methyl-2-octenoic acid, octanoic acid, 2-methyloctanoic acid, 3-methyloctanoic acid, 3-hydroxyoctanoic acid, 3-hydroxy-3-methyloctanoic acid, 2-nonenoic acid, 2-methyl-2-nonenoic acid, 3-methyl-2-nonenoic acid, nonanoic acid, 2-methylnonanoic acid, 3-methylnonanoic acid, 3-hydroxynonanoic acid, 3-hydroxy-3-methylnonanoic acid, 2-decenoic acid, 2-methyl-2-decenoic acid, 3-methyl-2-decenoic acid, decanoic acid, 2-methyldecanoic acid, 3-methyldecanoic acid, 3-hydroxydecanoic acid, 3-hydroxy-3-methyldecanoic acid, 10-hydroxydecanoic acid, 2-undecenoic acid, 2-methyl-2-undecenoic acid, 3-methyl-2-undecenoic acid, undecanoic acid, 2-methylundecanoic acid, 3-methylundecanoic acid, 3-hydroxyundecanoic acid, 3-hydroxy-3-methylundecanoic acid, dodecanoic acid, 2-hydroxydodecanoic acid, tridecanoic acid, or mixtures thereof;
sulfanylalkanols or mercaptoalkanols;
conjugated products of 3-methyl-3-sulfanylhexan-1-ol;
sulfo-conjugated steroids; or
mixtures thereof; and
v) optionally at least one basifying agent and/or at least one acid; and
B) subsequently removing the at least one template molecule to form vacant cavities that are complementary to the at least one template molecule.

2. The cosmetic composition according to claim 1, wherein the total amount of the at least one antiperspirant active agent, if present, ranges from 0.001% to 30% by weight, relative to the total weight of the composition, or the total amount of the at least one additional deodorant active agent other than the at least one molecularly imprinted polymer, if present, ranges from 0.01% to 10% by weight, relative to the total weight of the composition.

3. The composition according to claim 1, wherein the composition is:
a) in pressurized form in an aerosol device or in a pump-dispenser bottle;
b) in a device equipped with a perforated wall or a grate;
c) in a device equipped with a ball applicator;
d) in the form of a wand; or
e) in the form of a loose or compacted powder;
wherein the composition further comprises a physiologically acceptable medium.

4. The cosmetic composition according to claim 1, wherein the at least one template molecule further comprises a steroid.

5. The cosmetic composition according to claim 1, wherein the at least one template molecule further comprises a branched, saturated, and/or unsaturated aliphatic volatile fatty acid.

6. The cosmetic composition according to claim 1, wherein the at least one template molecule is a linear or branched, saturated or unsaturated, and/or optionally substituted C2-C13 aliphatic acid chosen from acetic acid, 2-propenoic acid, propanoic acid, 2-methylpropanoic acid, 2-methylpropenoic acid, 2-butenoic acid, 2-methyl-2-butenoic acid, 3-methyl-2-butenoic acid, butanoic acid, 2-methylbutanoic acid, 3-methylbutanoic acid, 3-hydroxybutanoic acid, 3-hydroxy-3-methylbutanoic acid, 2-pentenoic acid, 2-methyl-2-pentenoic acid, 3-methyl-2-pentenoic acid, pentanoic acid, 2-methylpentanoic acid, 3-methylpentanoic acid, 3-hydroxypentanoic acid, 3-hydroxy-3-methylpentanoic acid, 3-methyl-2-hexenoic acid, 3-hydroxy-3-methylhexanoic acid, 3-hydroxy-4-methyloctanoic acid, 3-hydroxyhexanoic acid, 2-heptenoic acid, 2-methyl-2-heptenoic acid, 3-methyl-2-heptenoic acid, heptanoic acid, 2-methylheptanoic acid, 3-methylheptanoic acid, 3-hydroxyheptanoic acid, 3-hydroxy-3-methylheptanoic acid, 2-octenoic acid, 2-methyl-2-octenoic acid, 3-methyl-2-octenoic acid, octanoic acid, 2-methyloctanoic acid, 3-methyloctanoic acid, 3-hydroxyoctanoic acid, 3-hydroxy-3-methyloctanoic acid, 2-nonenoic acid, 2-methyl-2-nonenoic acid, 3-methyl-2-nonenoic acid, nonanoic acid, 2-methylnonanoic acid, 3-methylnonanoic acid, 3-hydroxynonanoic acid, 3-hydroxy-3-methylnonanoic acid, 2-decenoic acid, 2-methyl-2-decenoic acid, 3-methyl-2-decenoic acid, decanoic acid, 2-methyldecanoic acid, 3-methyldecanoic acid, 3-hydroxydecanoic acid, 3-hydroxy-3-methyldecanoic acid, 10-hydroxydecanoic acid, 2-undecenoic acid, 2-methyl-2-undecenoic acid, 3-methyl-2-undecenoic acid, undecanoic acid, 2-methylundecanoic acid, 3-methylundecanoic acid, 3-hydroxyundecanoic acid, 3-hydroxy-3-methylundecanoic acid, dodecanoic acid, 2-hydroxydodecanoic acid, tridecanoic acid, or mixtures thereof.

7. The cosmetic composition according to claim 1, wherein the at least one template molecule is a sulfanylalkanol or mercaptoalkanol.

8. The cosmetic composition according to claim 1, wherein the at least one template molecule further comprises an amino acid.

9. The cosmetic composition according to claim 1, wherein the at least one template molecule further comprises an acid ester.

10. The cosmetic composition according to claim 1, wherein the at least one template molecule is a conjugated product of 3-methyl-3-sulfanylhexan-1-ol.

11. The cosmetic composition according to claim 1, wherein the at least one template molecule is a sulfo-conjugated steroid.

12. The cosmetic composition according to claim 1, wherein the composition further comprises a bacteriostatic agent or bactericidal agent.

13. The cosmetic composition according to claim 1, wherein the composition further comprises a zinc salt.

14. The cosmetic composition according to claim 1, wherein the composition comprises an odor absorber selected form the group consisting of zeolites, cyclodextrins, metal oxide silicates, metal oxide particles modified with a transition metal, aluminosilicates, and chitosan-based particles.

15. The cosmetic composition according to claim 1, wherein the composition comprises at least one substance which blocks enzymatic reactions responsible for the formation of odorous compounds selected from the group consisting of arylsulfatase, 5-lipoxygenase, am inocylase, and 13-glucuronidase inhibitors.

16. The cosmetic composition according to claim 1, having a pH ranging from 3 to 9.

17. The cosmetic composition according to claim 1, further comprising at least one excipient chosen from emulsifiers, oils, structuring agents, waxes, pasty compounds, gelling agents, thickeners, suspension agents, or propellants.

18. A composition for reducing body odor, the composition comprising:
a physiologically acceptable medium chosen from water, organic solvents, or mixtures thereof,
at least one excipient chosen from emulsifiers, oils, structuring agents, waxes, pasty compounds, gelling agents, thickeners, suspension agents, or propellants,
at least one molecularly imprinted polymer configured to trap at least one molecule at the surface of keratin materials in order to reduce body odor, and
at least one additional agent for reducing body odor chosen from antiperspirant active agents or deodorant active agents other than the at least one molecularly imprinted polymer,
wherein the pH of the composition ranges from 3 to 9, and
wherein the at least one molecularly imprinted polymer is obtained by:
A) sol-gel polymerization of a mixture comprising:
i) at least one functional silane monomer chosen from those of formulae (I) or

 (I)

in which:
$R_1$ is a linear or branched, saturated or unsaturated, cyclic or acyclic C1-C6 hydrocarbon-based chain, optionally substituted with a group chosen from:
amine $NH_2$ or NHR with R representing a $C_1$-$C_4$ alkyl group,
an aryl or aryloxy group, which is optionally substituted with an amino group or with a $C_1$-$C_4$ aminoalkyl group,
with the provisos that: Ri is optionally interrupted in its chain with a heteroatom, a carbonyl group —C(O)— or a combination thereof; and $R_1$ is linked to the silicon atom directly via a carbon atom,
R2 and R3, which are identical or different, are a linear or branched alkyl group comprising from 1 to 6 carbon atoms,
z denotes an integer ranging from 1 to 3, and
x denotes an integer ranging from 0 to 2, with z+x =3;
or

 (II)

in which:
$R_8$ and $R'_8$, which are identical or different, are i) a hydrogen atom or ii) a linear or branched, optionally substituted ($C_1$-$C_8$)alkyl group, and
$R_9$ is i) a hydrogen atom, ii) a group $OR_8$, iii) a linear or branched ($C_1$-$C_6$)alkyl group, optionally substituted with a thiol or hydroxyl group or with an amino group $N(H)R_d$ with $R_d$ representing a hydrogen atom or a ($C_1$-$C_6$)alkyl group, iv) a (hetero)aryl group, or v) (hetero)aryl($C_1$-$C_6$)alkyl,
z=1, 2, or 3, and
x=0, 1, or 2,
with z+x=3;
ii) at least one tetra($C_1$-$C_6$)alkoxysilane crosslinking agent;
iii) at least porogenic solvent chosen from polar protic solvents and polar aprotic solvents;
iv) at least one template molecule chosen from:
linear or branched, saturated or unsaturated, and/or optionally substituted C2-C13 aliphatic acids chosen from acetic acid, 2-propenoic acid, propanoic acid, 2-methylpropanoic acid, 2-methylpropenoic acid, 2-butenoic acid, 2-methyl-2-butenoic acid, 3-methyl-2-butenoic acid, butanoic acid, 2-methylbutanoic acid, 3-methylbutanoic acid, 3-hydroxybutanoic acid, 3-hydroxy-3-methylbutanoic acid, 2-pentenoic acid, 2-methyl-2-pentenoic acid, 3-methyl-2-pentenoic acid, pentanoic acid, 2-methylpentanoic acid, 3-methylpentanoic acid, 3-hydroxypentanoic acid, 3-hydroxy-3-methylpentanoic acid, 3-methyl-2-hexenoic acid, 3-hydroxy-3-methylhexanoic acid, 3-hydroxy-4-methyloctanoic acid, 3-hydroxyhexanoic acid, 2-heptenoic acid, 2-methyl-2-heptenoic acid, 3-methyl-2-heptenoic acid, heptanoic acid, 2-methylheptanoic acid, 3-methylheptanoic acid, 3-hydroxyheptanoic acid, 3-hydroxy-3-methylheptanoic acid, 2-octenoic acid, 2-methyl-2-octenoic acid, 3-methyl-2-octenoic acid, octanoic acid, 2-methyloctanoic acid, 3-methyloctanoic acid, 3-hydroxyoctanoic acid, 3-hydroxy-3-methyloctanoic acid, 2-nonenoic acid, 2-methyl-2-nonenoic acid, 3-methyl-2-nonenoic acid, nonanoic acid, 2-methylnonanoic acid, 3-methylnonanoic acid, 3-hydroxynonanoic acid, 3-hydroxy-3-methylnonanoic acid, 2-decenoic acid, 2-methyl-2-decenoic acid, 3-methyl-2-decenoic acid, decanoic acid, 2-methyldecanoic acid, 3-methyldecanoic acid, 3-hydroxydecanoic acid, 3-hydroxy-3-methyldecanoic acid, 10-hydroxydecanoic acid, 2-undecenoic acid, 2-methyl-2-undecenoic acid, 3-methyl-2-undecenoic acid, undecanoic acid, 2-methylundecanoic acid, 3-methylundecanoic acid, 3-hydroxyundecanoic acid, 3-hydroxy-3-methylundecanoic acid, dodecanoic acid, 2-hydroxydodecanoic acid, tridecanoic acid, or mixtures thereof;
sulfanylalkanols or mercaptoalkanols;
conjugated products of 3-methyl-3-sulfanylhexan-1-ol;
sulfo-conjugated steroids; or mixtures thereof;
v) at least one basifying agent; and
vi) optionally at least one acid; and
B) subsequently removing the at least one template molecule to form vacant cavities that are complementary to the at least one template molecule.

19. A composition for reducing body odor, the composition comprising:
a physiologically acceptable medium chosen from water, organic solvents, or mixtures thereof,
at least one excipient chosen from emulsifiers, oils, structuring agents, waxes, pasty compounds, gelling agents, thickeners, suspension agents, or propellants,
at least one molecularly imprinted polymer configured to trap at least one molecule at the surface of keratin materials in order to reduce body odor, and
at least one additional agent for reducing body odor chosen from antiperspirant active agents or deodorant active agents other than the at least one molecularly imprinted polymer, wherein the pH of the composition ranges from 3 to 9, and wherein the at least one molecularly imprinted polymer is obtained by:
- A) sol-gel polymerization of a mixture comprising:
  - i) aminopropyltriethoxysilane (APTES);
  - ii) tetraethoxysilane (TEOS);
  - iii) ethanol;
  - iv) at least one template molecule chosen from acetic acid, 2-propenoic acid, propanoic acid, 2-methylpropanoic acid, 2-methylpropenoic acid, 2-butenoic acid, 2-methyl-2-butenoic acid, 3-methyl-2-butenoic acid, butanoic acid, 2-methylbutanoic acid, 3-methylbutanoic acid, 3-hydroxybutanoic acid, 3-hydroxy-3-methylbutanoic acid, 2-pentenoic acid, 2-methyl-2-pentenoic acid, 3-methyl-2-pentenoic acid, pentanoic acid, 2-methylpentanoic acid, 3-methylpentanoic acid, 3-hydroxypentanoic acid, 3-hydroxy-3-methylpentanoic acid, 3-methyl-2-hexenoic acid, 3-hydroxy-3-methylhexanoic acid, 3-hydroxy-4-methyloctanoic acid, 3-hydroxyhexanoic acid, 2-heptenoic acid, 2-methyl-2-heptenoic acid, 3-methyl-2-heptenoic acid, heptanoic acid, 2-methylheptanoic acid, 3-methylheptanoic acid, 3-hydroxyheptanoic acid, 3-hydroxy-3-methylheptanoic acid, 2-octenoic acid, 2-methyl-2-octenoic acid, 3-methyl-2-octenoic acid, octanoic acid, 2-methyloctanoic acid, 3-methyloctanoic acid, 3-hydroxyoctanoic acid, 3-hydroxy-3-methyloctanoic acid, 2-nonenoic acid, 2-methyl-2-nonenoic acid, 3-methyl-2-nonenoic acid, nonanoic acid, 2-methylnonanoic acid, 3-methylnonanoic acid, 3-hydroxynonanoic acid, 3-hydroxy-3-methylnonanoic acid, 2-decenoic acid, 2-methyl-2-decenoic acid, 3-methyl-2-decenoic acid, decanoic acid, 2-methyldecanoic acid, 3-methyldecanoic acid, 3-hydroxydecanoic acid, 3-hydroxy-3-methyldecanoic acid, 10-hydroxydecanoic acid, 2-undecenoic acid, 2-methyl-2-undecenoic acid, 3-methyl-2-undecenoic acid, undecanoic acid, 2-methylundecanoic acid, 3-methylundecanoic acid, 3-hydroxyundecanoic acid, 3-hydroxy-3-methylundecanoic acid, dodecanoic acid, 2-hydroxydodecanoic acid, tridecanoic acid, or mixtures thereof;
  - v) at least one basifying agent; and
  - vi) optionally at least one acid; and
- B) subsequently removing the at least one template molecule to form vacant cavities that are complementary to the at least one template molecule.

* * * * *

UNITED STATES PATENT AND TRADEMARK OFFICE
CERTIFICATE OF CORRECTION

| | | |
|---|---|---|
| PATENT NO. | : 11,246,823 B2 | Page 1 of 1 |
| APPLICATION NO. | : 14/655386 | |
| DATED | : February 15, 2022 | |
| INVENTOR(S) | : Andrew Greaves et al. | |

It is certified that error appears in the above-identified patent and that said Letters Patent is hereby corrected as shown below:

On the Title Page

Item (57) Abstract, Line 9, after "concerns a" delete "NI";

In the Claims

Column 29, Claim 18, Line 38, please change "Ri" to -- R1 --.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*